United States Patent
Wild et al.

(10) Patent No.: US 6,605,427 B2
(45) Date of Patent: Aug. 12, 2003

(54) ASSAY FOR DETECTION OF VIRAL FUSION INHIBITORS

(75) Inventors: Carl T. Wild, Gaithersburg, MD (US); Graham P. Allaway, Darnestown, MD (US)

(73) Assignee: Panacos Pharmaceuticals, Inc., Gaithersburg, MD (US)

(*) Notice: Subject to any disclaimer, the term of this patent is extended or adjusted under 35 U.S.C. 154(b) by 0 days.

(21) Appl. No.: 09/779,451

(22) Filed: Feb. 9, 2001

(65) Prior Publication Data

US 2002/0094521 A1 Jul. 18, 2002

Related U.S. Application Data

(60) Provisional application No. 60/235,901, filed on Sep. 28, 2000, and provisional application No. 60/181,543, filed on Feb. 10, 2000.

(51) Int. Cl.[7] .................. C12Q 1/70; C12Q 1/68; C12Q 1/06; C12N 5/00; C12N 5/06
(52) U.S. Cl. .................. 435/5; 435/6; 435/39; 435/325; 435/334; 435/339.1
(58) Field of Search .................. 435/5, 6, 39, 325, 435/334, 339.1

(56) References Cited

U.S. PATENT DOCUMENTS

| 5,444,044 A | 8/1995 | Jiang et al. ............. 514/12 |
| 5,464,933 A | 11/1995 | Bolognesi et al. ......... 530/324 |
| 5,656,480 A | 8/1997 | Wild et al. .............. 435/325 |
| 5,817,767 A | 10/1998 | Allaway et al. .......... 530/387.3 |
| 5,840,843 A | 11/1998 | Jiang et al. ............. 530/350 |
| 6,008,044 A | 12/1999 | Cotropia ............... 435/339.1 |
| 6,013,263 A | 1/2000 | Barney et al. ........... 424/212.1 |
| 6,015,881 A | 1/2000 | Kang et al. ............. 530/339 |
| 6,017,536 A | 1/2000 | Barney et al. ........... 424/188.1 |

FOREIGN PATENT DOCUMENTS

| WO | WO 88/08429 | 11/1988 |
| WO | WO 91/09872 | 7/1991 |
| WO | WO 92/19742 | 11/1992 |
| WO | WO 94/02505 | 2/1994 |
| WO | WO 94/28920 | 12/1994 |
| WO | WO 95/21912 | 8/1995 |
| WO | WO 96/12023 | 4/1996 |
| WO | WO 96/19495 | 6/1996 |
| WO | WO 96/40191 | 12/1996 |
| WO | WO 00/06599 | 2/2000 |
| WO | WO 00/40616 | 7/2000 |

OTHER PUBLICATIONS

Chen, C.–H. et al., "Monoclonal Antibodies That Bind to the Core of Fusion–Active Glycoprotein 41," *AIDS Res. Hum. Retroviruses* 16:2037–2041, Mary Ann Liebert, Inc., Publishers (Dec. 2000).

(List continued on next page.)

*Primary Examiner*—Hankyel T. Park
(74) *Attorney, Agent, or Firm*—Sterne, Kessler, Goldstein & Fox PLLC

(57) ABSTRACT

The invention is directed to a methods for identifying compounds that inhibit or prevent infection of cells by enveloped viruses such as HIV-1 by preventing or disrupting conformational changes in the viral transmembrane protein that are required for virus fusion with those cells, and the compounds discovered by such methods. The invention also includes using these assays as diagnostic assays to detect antibodies in virus infected individuals that inhibit the viral entry processes.

19 Claims, 11 Drawing Sheets

OTHER PUBLICATIONS

Eckert, D.M. et al., "Inhibiting HIV–1 Entry: Discovery of D–Peptide Inhibitors that Target the gp41 Coiled–Coil Pocket," *Cell* 99:103–115, Cell Press (Oct. 1999).

Ferrer, M. et al., "Selection of gp41–mediated HIV–1 cell entry inhibitors from biased combinatorial libraries of non–natural binding elements," *Nat. Struct. Biol.* 6:953–959, Nature Publishing Group (Oct. 1999).

Ryu, J.–R. et al., "Development of an in vitro Assay system for Screening of gp41 Inhibitory Compounds," *Mol. Cells* 8:717–723, Springer–Verlag (1998).

International Search Report of International Application No. PCT/US 01/04030, mailed Aug. 22, 2001.

Alkhatib, G., et al., "CC CKR5: A RANTES, MIP–1α, MIP–1β Receptor as a Fusion Cofactor for Macrophage–Tropic HIV–1," *Science* 272:1955–1958, Association for the Advancement of Science (Jun. 1996).

Allan, J.S., et al., "Strong Association of Simian Immunodeficiency Virus (SIVagm) Envelope Glycoprotein Heterodimers: Possible Role in Receptor–Mediated Activation," *AIDS Res. Hum. Retroviruses* 8:2011–2020, Mary Ann Leibert, Inc., Publishers (Dec. 1992).

Arthos, J., et al., "Identification of the Residues in Human CD4 Critical for the Binding of HIV," *Cell* 5:469–481, Cell Press (May 1989).

Barin, F., et al., "Virus Envelope Protein of HTLV–III Represents Major Target Antigen for Antibodies in AIDS Patients," *Science* 228:1094–1096, Association for the Advancement of Science (May 1985).

Bosch, M.L., et al., "Identification of the Fusion Peptide of Primate Immunodeficiency Viruses," *Science* 244:694–697, Association for the Advancement of Science (May 1989).

Broder, C.C., and Dimitrov, D.S., "HIV and the 7–Transmembrane Domain Receptors," *Pathobiol.* 64:171–179, Karger (1996).

Calderone, T.L., et al., "High–level Misincorporation of Lysine for Arginine at AGA Codons in a Fusion Protein Expressed in *Escherichia coli*," *J. Mol. Biol.* 262:407–412, Academic Press, Inc. (Oct. 1996).

Chan, D.C., and Kim, P.S., "HIV Entry and Its Inhibition," *Cell* 93:681–684, Cell Press (May 1998).

Chan, D.C., et al., "Core Structure of gp41 from the HIV Envelope Glycoprotein," *Cell* 89:263–273, Cell Press (Apr. 1997).

Chen, C–H., et al., "A Molecular Clasp in the Human Immunodeficiency Virus (HIV) Type 1 TM Protein Determines the Anti–HIV Activity of gp41 Derivatives: Implication for Viral Fusion," *J. Virol.* 69:3771–3777, American Society for Microbiology (Jun. 1995).

Choe, H., et al., "The β–Chemokine Receptors CCR3 and CCR5 Facilitate Infection by Primary HIV–1 Isolates," *Cell* 85:1135–1148, Cell Press (Jun. 1996).

Clapham, P.R., et al., "Human Immunodeficiency Virus Type 2 Infection and Fusion of CD4–Negative Human Cell Lines: Induction and Enhancement by Soluble CD4," *J. Virol.* 66:3531–3537, American Society for Microbiology (Jun. 1992).

Dalgleish, A.G., et al., "The CD4 (T4) antigen is an essential component of the receptor for the AIDS retrovirus," *Nature* 312:763–767, Macmillan Publishers Ltd. (Dec. 1984).

Delwart, E.L., et al., "Retroviral Envelope Glycoproteins Contain a 'Leucine Zipper'–like Repeat," *AIDS Res. Hum. Retroviruses* 6:703–706, Mary Ann Leibert, Inc., Publishers (1990).

Deng, H., et al., "Identification of a major co–receptor for primary isolates of HIV–1," *Nature* 381:661–666, Macmillan Publishers Ltd. (Jun. 1996).

Dimitrov, D.S., "Fusin—a place for HIV–1 and T4 cells to meet," *Nat. Med.* 2:640–641, Nature Publishing Company (Jun. 1996).

Donzella, G.A., et al., "AMD3100, a small molecule inhibitor of HIV–1 entry via the CXCR4 co–receptor," *Nat. Med.* 4:72–77, Nature Publishing Company (Jan. 1998).

Doranz, B.J., et al., "A Dual–Tropic Primary HIV–1 Isolate That Uses Fusin and the β–Chemokine Receptors CKR–5, CKR–3, and CKR–2b as Fusion Cofactors," *Cell* 85:1149–1158, Cell Press (Jun. 1996).

Dragic, T., et al., "HIV–1 entry into $CD4^+$ cells is mediated by the chemokine receptor CC–CKR–5," *Nature* 381:667–673, Macmillan Publishers Ltd. (Jun. 1996).

Earl, P.L., et al., "Epitope Map of Human Immunodeficiency Virus Type 1 gp41 Derived from 47 Monoclonal Antibodies Produced by Immunization with Oligomeric Envelope Protein," *J. Virol.* 71:2674–2684, American Society for Microbiology (Apr. 1997).

Eiden, L.E., and Lifson, J.D., "HIV Interactions with CD4: a continuum of conformations and consequences," *Immunol. Today* 13:201–206, Elsevier Science Publishers Ltd. (1992).

Feng, Y., et al., "HIV–1 Entry Cofactor: Functional cDNA Cloning of a Seven–Transmembrane, G Protein–Coupled Receptor," *Science* 272:872–877, Association for the Advancement of Science (May 1996).

Folks, T.M., et al., "Biological and Biochemical Characterization of a Cloned Leu–3⁻ Cell Surviving Infection with the Acquired Immune Deficiency Syndrome Retrovirus," *J. Exp. Med.* 164:280–290, The Rockefeller University Press (Jul. 1986).

Freed, E.O., et al., "Characterization of the fusion domain of the human immunodeficiency virus type 1 envelope glycoprotein gp41," *Proc. Natl. Acad. Sci. USA* 87:4650–4654, National Academy of Sciences of the USA (Jun. 1990).

Furata, R.A., et al., "Capture of an early fusion–active conformation of HIV–1 gp41," *Nat. Struct. Biol.* 5:276–279, Nature Publishing Company (Apr. 1998).

Gallaher, W.R., et al., "A General Model for the Transmembrane Proteins of HIV and Other Retroviruses," *AIDS Res. Hum. Retroviruses* 5:431–440, Mary Ann Leibert, Inc., Publishers (Aug. 1989).

Gendelman, H.E., et al., "Molecular Characterization of a Polymerase Mutant Human Immunodeficiency Virus," *Virol.* 160:323–329, Academic Press (Oct. 1987).

Haddrick, M., et al., "Production of non–infectious human immunodeficiency virus–like particles which package specifically viral RNA," *J. Virol. Meth.* 61:89–93, Elsevier Science (Sep. 1996).

Jiang, S., et al., "A Conformation–Specific Monoclonal Antibody Reacting with Fusion–Active gp41 from the Human Immunodeficiency Virus Type 1 Envelope Glycoprotein," *J. Virol.* 72:10213–10217, American Society for Microbiology (Dec. 1998).

Jiang, S., et al., "A screening assay for antiviral compounds targeted to the HIV–1 gp41 core structure using a conformation–specific monoclonal antibody," *J. Virol. Meth.* 80:85–96, Elsevier Science (Jun. 1999).

Kemble, G.W., et al., "Intermonomer Disulfide Bonds Impair the Fusion Activity of Influenza Virus Hemagglutinin," *J. Virol.* 66:4940–4950, American Society for Microbiology (Aug. 1992).

LaCasse, R.A., et al., "Fusion–Competent Vaccines: Broad Neutralization of Primary Isolates of HIV," *Science* 283:357–362, Association for the Advancement of Science (Jan. 1999).

Lambert, D.M., et al., "Peptides from conserved regions of paramyxovirus fusion (F) proteins are potent inhibitors of viral fusion," *Proc. Natl. Acad. Sci. USA* 93:2186–2191, National Academy of Sciences of the USA (Mar. 1996).

Lifson, J.D., et al., "Induction of CD4–dependent cell fusion by the HTLV–III/LAV envelope glycoprotein," *Nature* 323:725–728, Macmillan Publishers Ltd. (Oct. 1986).

Lifson, J.D., et al., "AIDS Retrovirus Induced Cytopathology: Giant Cell Formation and Involvement of CD4 Antigen," *Science* 232:1123–1127, Association for the Advancement of Science (May 1986).

Lightfoote, M.M., et al., "Structural Characterization of Reverse Transcriptase and Endonuclease Polypeptides of the Acquired Immunodeficiency Syndrome Retrovirus," *J. Virol.* 60:771–775, American Society for Microbiology (Nov. 1986).

Lu, M., et al., "A trimeric structural domain of the HIV–1 transmembrane glycoprotein," *Nat. Struct. Biol.* 2:1075–1082, Nature Publishing Company (Dec. 1995).

McDougal, J.S., et al., "Binding of HTLV–III/LAV to T4$^+$ T Cells by a Complex of the 110K Viral Protein and the T4 Molecule," *Science* 231:382–385, Association for the Advancement of Science (Jan. 1986).

Muster, T., et al., "A Conserved Neutralizing Epitope on gp41 of Human Immunodeficiency Virus Type 1," *J. Virol.* 67:6642–6647, American Society for Microbiology (Nov. 1993).

Muster, T., et al., "Cross–Neutralizing Activity against Divergent Human Immunodeficiency Virus Type 1 Isolates Induced by the gp41 Sequence ELDKWAS," *J. Virol.* 68:4031–4034, American Society for Microbiology (Jun. 1994).

Sattentau, Q.J. and Moore, J.P., "Conformational Changes Induced in the Human Immunodeficiency Virus Envelope Glycoprotein by Soluble CD4 Binding," *J. Exp. Med.* 174:407–415, The Rockefeller University Press (Aug. 1991).

Sattentau, Q.J., and Moore, J.P., "Human Immunodeficiency Virus Type 1 Neutralization Is Determined by Epitope Exposure on the gp120 Oligomer," *J. Exp. Med.* 182:185–196, The Rockefeller University Press (Jul. 1995).

Slepushkin, V.A., et al., "Investigation of Human Immunodeficiency Virus Fusion Peptides. Analysis of Interrelations Between Their Structure and Function," *AIDS Res. Hum. Retroviruses* 8:9–18, Mary Ann Leibert, Inc., Publishers (Jan. 1992).

VanCott, T.C., et al., "Antibodies with Specificity to Native gp120 and Neutralization Activity against Primary Human Immunodeficiency Virus Type 1 Isolates Elicited by Immunization with Oligomeric gp160," *J. Virol.* 71:4319–4330, American Society for Microbiology (Jun. 1997).

Weissenhorn, W., et al., "Atomic structure of the ectodomain from HIV–1 gp41," *Nature* 387:426–430, Macmillan Publishers Ltd. (May 1997).

White, J.M., and Wilson, I.A., "Anti–Peptide Antibodies Detect Steps in a Protein Conformational Change: Low–pH Activation of the Influenza Virus Hemagglutinin," *J. Cell Biol.* 105:2887–2896, The Rockefeller University Press, Inc. (Dec. 1987).

Wild, C., et al., "A synthetic peptide inhibitor of human immunodeficiency virus replication: Correlation between solution structure and viral inhibition," *Proc. Natl. Acad. Sci. USA* 89:10537–10541, National Academy of Sciences of the USA (Nov. 1992).

Wild, C., et al., "A Synthetic Peptide from HIV–1 gp41 Is a Potent Inhibitor of Virus–Mediated Cell–Cell Fusion," *AIDS Res. Hum. Retroviruses* 9:1051–1053, Mary Ann Leibert, Inc., Publishers (Nov. 1993).

Wild, C., et al., "Peptides corresponding to a predictive α–helical domain of human immunodeficiency virus type 1 gp41 are potent inhibitors of virus infection," *Proc. Natl. Acad. Sci. USA* 91:9770–9774, National Academy of Sciences of the USA (Oct. 1994).

Wild, C., et al., "Propensity for a leucine zipper–like domain of human immunodeficiency virus type 1 gp41 to form oligomers correlates with a role in virus–induced fusion rather than assembly of the glycoprotein complex," *Proc. Natl. Acad. Sci. USA* 91:12676–12680, National Academy of Sciences of the USA (Dec. 1994).

Wild, C., et al., "The Inhibitory Activity of an HIV Type 1 Peptide Correlates with Its Ability to Interact with a Leucine Zipper Structure," *AIDS Res. Hum. Retroviruses* 11:323–325, Mary Ann Leibert, Inc., Publishers (Mar. 1995).

Xu, J–Y., et al., "Epitope Mapping of Two Immunodominant Domains of gp41, the Transmembrane Protein of Human Immunodeficiency Virus Type 1, Using Ten Human Monoclonal Antibodies," *J. Virol.* 65:4832–4838, American Society for Microbiology (Sep. 1991).

Co–pending U.S. patent application Ser. No. 09/480,336 filed Jan. 7, 2000.

Gnann, J.W., Jr., et al., "Fine Mapping of an Immunodominant Domain in the Transmembrane Glycoprotein of Human Immunodeficency Virus," *J. Virol.* 61:2639–2641, American Society for Microbiology (Aug. 1987).

Norrby, E., et al., "Discrimination between antibodies to HIV and to related retroviruses using site–directed serology," *Nature* 329:248–250, Macmillan Publishers Ltd. (Sep. 1987).

Yamshchikov, G.V., et al., "Assembly of SIV Virus–like Particles Containing Envelope Proteins Using a Baculovirus Expression System," *Virol.* 214:50–58, Academic Press, Inc. (Dec. 1995).

SEQUENCE LISTING

<160> NUMBER OF SEQ ID NOS: 77

<210> SEQ ID NO 1
<211> LENGTH: 55
<212> TYPE: PRT
<213> ORGANISM: Human immunodeficiency virus type 1

<400> SEQUENCE: 1

Ala Arg Gln Leu Leu Ser Gly Ile Val Gln Gln Gln Asn Asn Leu Leu
1               5                   10                  15

Arg Ala Ile Glu Ala Gln Gln His Leu Leu Gln Leu Thr Val Trp Gly
            20                  25                  30

Ile Lys Gln Leu Gln Ala Arg Ile Leu Ala Val Glu Arg Tyr Leu Lys
        35                  40                  45

Asp Gln Gln Leu Leu Gly Ile
    50                  55

<210> SEQ ID NO 2

```
<211> LENGTH: 38
<212> TYPE: PRT
<213> ORGANISM: Human immunodeficiency virus type 1

<400> SEQUENCE: 2

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Lys Asp Gln
        35

<210> SEQ ID NO 3
<211> LENGTH: 36
<212> TYPE: PRT
<213> ORGANISM: Human immunodeficiency virus type 1

<400> SEQUENCE: 3

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu
        35

<210> SEQ ID NO 4
<211> LENGTH: 56
<212> TYPE: PRT
<213> ORGANISM: Human immunodeficiency virus type 1

<400> SEQUENCE: 4

Trp Asn Asn Met Thr Trp Met Glu Trp Asp Arg Glu Ile Asn Asn Tyr
1               5                   10                  15

Thr Ser Leu Ile His Ser Leu Ile Glu Glu Ser Gln Asn Gln Gln Glu
            20                  25                  30

Lys Asn Glu Gln Glu Leu Leu Glu Leu Asp Lys Trp Ala Ser Leu Trp
        35                  40                  45

Asn Trp Phe Asn Ile Thr Asn Trp
    50                  55

<210> SEQ ID NO 5
<211> LENGTH: 36
<212> TYPE: PRT
<213> ORGANISM: Human immunodeficiency virus type 1

<400> SEQUENCE: 5

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 6
<211> LENGTH: 34
<212> TYPE: PRT
<213> ORGANISM: Human immunodeficiency virus type 1

<400> SEQUENCE: 6

Trp Met Glu Trp Asp Arg Glu Ile Asn Asn Tyr Thr Ser Leu Ile His
1               5                   10                  15
```

Ser Leu Ile Glu Glu Ser Gln Asn Gln Gln Lys Asn Gln Glu
            20                  25                  30

Leu Leu

<210> SEQ ID NO 7
<211> LENGTH: 5
<212> TYPE: PRT
<213> ORGANISM: Artificial Sequence
<220> FEATURE:
<221> NAME/KEY: REPEAT
<222> LOCATION: (1)..(5)
<223> OTHER INFORMATION: (GGGGS)x, where x is 1, 2, 3, 4, or 5
<221> NAME/KEY: misc_feature
<223> OTHER INFORMATION: Preferred amino acid residues

<400> SEQUENCE: 7

Gly Gly Gly Gly Ser
1               5

<210> SEQ ID NO 8
<211> LENGTH: 345
<212> TYPE: PRT
<213> ORGANISM: Human immunodeficiency virus type 1

<400> SEQUENCE: 8

Ala Val Gly Ile Gly Ala Leu Phe Leu Gly Phe Leu Gly Ala Ala Gly
1               5                   10                  15

Ser Thr Met Gly Ala Arg Ser Met Thr Leu Thr Val Gln Ala Arg Gln
            20                  25                  30

Leu Leu Ser Gly Ile Val Gln Gln Gln Asn Asn Leu Leu Arg Ala Ile
        35                  40                  45

Glu Ala Gln Gln His Leu Leu Gln Leu Thr Val Trp Gly Ile Lys Gln
    50                  55                  60

Leu Gln Ala Arg Ile Leu Ala Val Glu Arg Tyr Leu Lys Asp Gln Gln
65                  70                  75                  80

Leu Leu Gly Ile Trp Gly Cys Ser Gly Lys Leu Ile Cys Thr Thr Ala
                85                  90                  95

Val Pro Trp Asn Ala Ser Trp Ser Asn Lys Ser Leu Glu Gln Ile Trp
            100                 105                 110

Asn Asn Met Thr Trp Met Glu Trp Asp Arg Glu Ile Asn Asn Tyr Thr
        115                 120                 125

Ser Leu Ile His Ser Leu Ile Glu Glu Ser Gln Asn Gln Gln Glu Lys
    130                 135                 140

Asn Glu Gln Glu Leu Leu Glu Leu Asp Lys Trp Ala Ser Leu Trp Asn
145                 150                 155                 160

Trp Phe Asn Ile Thr Asn Trp Leu Trp Tyr Ile Lys Ile Phe Ile Met
                165                 170                 175

Ile Val Gly Gly Leu Val Gly Leu Arg Ile Val Phe Ala Val Leu Ser
            180                 185                 190

Ile Val Asn Arg Val Arg Gln Gly Tyr Ser Pro Leu Ser Phe Gln Thr
        195                 200                 205

His Leu Pro Thr Pro Arg Gly Pro Asp Arg Pro Glu Gly Ile Glu Glu
    210                 215                 220

Glu Gly Gly Glu Arg Asp Arg Asp Arg Ser Ile Arg Leu Val Asn Gly
225                 230                 235                 240

Ser Leu Ala Leu Ile Trp Asp Asp Leu Arg Ser Leu Cys Leu Phe Ser
                245                 250                 255

```
Tyr His Arg Leu Arg Asp Leu Leu Leu Ile Val Thr Arg Ile Val Glu
                260                 265                 270

Leu Leu Gly Arg Arg Gly Trp Glu Ala Leu Lys Tyr Trp Trp Asn Leu
            275                 280                 285

Leu Gln Tyr Trp Ser Gln Glu Leu Lys Asn Ser Ala Val Ser Leu Leu
        290                 295                 300

Asn Ala Thr Ala Ile Ala Val Ala Glu Gly Thr Asp Arg Val Ile Glu
305                 310                 315                 320

Val Val Gln Gly Ala Cys Arg Ala Ile Arg His Ile Pro Arg Arg Ile
                325                 330                 335

Arg Gln Gly Leu Glu Arg Ile Leu Leu
                340                 345

<210> SEQ ID NO 9
<211> LENGTH: 45
<212> TYPE: PRT
<213> ORGANISM: Human immunodeficiency virus type 1

<400> SEQUENCE: 9

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu Ala Val Glu Arg Tyr Leu Lys Asp Gln
        35                  40                  45

<210> SEQ ID NO 10
<211> LENGTH: 45
<212> TYPE: PRT
<213> ORGANISM: Human immunodeficiency virus type 1

<400> SEQUENCE: 10

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Val Leu Ala Leu Glu Arg Tyr Leu Arg Asp Gln
        35                  40                  45

<210> SEQ ID NO 11
<211> LENGTH: 36
<212> TYPE: PRT
<213> ORGANISM: Human immunodeficiency virus type 1

<400> SEQUENCE: 11

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Val Leu
        35

<210> SEQ ID NO 12
<211> LENGTH: 38
<212> TYPE: PRT
<213> ORGANISM: Human immunodeficiency virus type 1

<400> SEQUENCE: 12

Asn Asn Leu Leu Arg Ala Ile Glu Ala Gln Gln His Leu Leu Gln Leu
1               5                   10                  15
```

```
Thr Val Trp Gly Ile Lys Gln Leu Gln Ala Arg Val Leu Ala Leu Glu
         20                  25                  30

Arg Tyr Leu Arg Asp Gln
         35

<210> SEQ ID NO 13
<211> LENGTH: 45
<212> TYPE: PRT
<213> ORGANISM: Human immunodeficiency virus type 1

<400> SEQUENCE: 13

Ser Gly Ile Val Gln Gln Gln Asn Asn Leu Leu Arg Ala Ile Glu Ala
1               5                   10                  15

Gln Gln Arg Met Leu Gln Leu Thr Val Trp Gly Ile Lys Gln Leu Gln
            20                  25                  30

Ala Arg Val Leu Ala Val Glu Arg Tyr Leu Gly Asp Gln
        35                  40                  45

<210> SEQ ID NO 14
<211> LENGTH: 36
<212> TYPE: PRT
<213> ORGANISM: Human immunodeficiency virus type 1

<400> SEQUENCE: 14

Ser Gly Ile Val Gln Gln Gln Asn Asn Leu Leu Arg Ala Ile Glu Ala
1               5                   10                  15

Gln Gln Arg Met Leu Gln Leu Thr Val Trp Gly Ile Lys Gln Leu Gln
            20                  25                  30

Ala Arg Val Leu
        35

<210> SEQ ID NO 15
<211> LENGTH: 38
<212> TYPE: PRT
<213> ORGANISM: Human immunodeficiency virus type 1

<400> SEQUENCE: 15

Asn Asn Leu Leu Arg Ala Ile Glu Ala Gln Gln Arg Met Leu Gln Leu
1               5                   10                  15

Thr Val Trp Gly Ile Lys Gln Leu Gln Ala Arg Val Leu Ala Val Glu
            20                  25                  30

Arg Tyr Leu Gly Asp Gln
        35

<210> SEQ ID NO 16
<211> LENGTH: 45
<212> TYPE: PRT
<213> ORGANISM: Human immunodeficiency virus type 1

<400> SEQUENCE: 16

Ser Gly Ile Val Gln Gln Gln Asn Asn Leu Leu Arg Ala Ile Glu Ala
1               5                   10                  15

Gln Gln His Met Leu Gln Leu Thr Val Trp Gly Ile Lys Gln Leu Gln
            20                  25                  30

Ala Arg Val Leu Ala Leu Glu Arg Tyr Leu Arg Asp Gln
        35                  40                  45

<210> SEQ ID NO 17
<211> LENGTH: 36
<212> TYPE: PRT
```

```
<213> ORGANISM: Human immunodeficiency virus type 1

<400> SEQUENCE: 17

Ser Gly Ile Val Gln Gln Gln Asn Asn Leu Leu Arg Ala Ile Glu Ala
1               5                   10                  15

Gln Gln His Met Leu Gln Leu Thr Val Trp Gly Ile Lys Gln Leu Gln
                20                  25                  30

Ala Arg Val Leu
            35

<210> SEQ ID NO 18
<211> LENGTH: 38
<212> TYPE: PRT
<213> ORGANISM: Human immunodeficiency virus type 1

<400> SEQUENCE: 18

Asn Asn Leu Leu Arg Ala Ile Glu Ala Gln Gln His Met Leu Gln Leu
1               5                   10                  15

Thr Val Trp Gly Ile Lys Gln Leu Gln Ala Arg Val Leu Ala Leu Glu
                20                  25                  30

Arg Tyr Leu Arg Asp Gln
            35

<210> SEQ ID NO 19
<211> LENGTH: 45
<212> TYPE: PRT
<213> ORGANISM: Human immunodeficiency virus type 1

<400> SEQUENCE: 19

Ser Gly Ile Val Gln Gln Gln Ser Asn Leu Leu Arg Ala Ile Glu Ala
1               5                   10                  15

Gln Gln His Met Leu Gln Leu Thr Val Trp Gly Ile Lys Gln Leu Gln
                20                  25                  30

Ala Arg Val Leu Ala Ile Glu Arg Tyr Leu Arg Asp Gln
            35                  40                  45

<210> SEQ ID NO 20
<211> LENGTH: 36
<212> TYPE: PRT
<213> ORGANISM: Human immunodeficiency virus type 1

<400> SEQUENCE: 20

Ser Gly Ile Val Gln Gln Gln Ser Asn Leu Leu Arg Ala Ile Glu Ala
1               5                   10                  15

Gln Gln His Met Leu Gln Leu Thr Val Trp Gly Ile Lys Gln Leu Gln
                20                  25                  30

Ala Arg Val Leu
            35

<210> SEQ ID NO 21
<211> LENGTH: 38
<212> TYPE: PRT
<213> ORGANISM: Human immunodeficiency virus type 1

<400> SEQUENCE: 21

Ser Asn Leu Leu Arg Ala Ile Glu Ala Gln Gln His Met Leu Gln Leu
1               5                   10                  15

Thr Val Trp Gly Ile Lys Gln Leu Gln Ala Arg Val Leu Ala Ile Glu
                20                  25                  30

Arg Tyr Leu Arg Asp Gln
```

<210> SEQ ID NO 22
<211> LENGTH: 45
<212> TYPE: PRT
<213> ORGANISM: Human immunodeficiency virus type 1

<400> SEQUENCE: 22

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Val Leu Ala Val Glu Ser Tyr Leu Lys Asp Gln
        35                  40                  45

<210> SEQ ID NO 23
<211> LENGTH: 38
<212> TYPE: PRT
<213> ORGANISM: Human immunodeficiency virus type 1

<400> SEQUENCE: 23

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Val Leu Ala Val Glu
            20                  25                  30

Ser Tyr Leu Lys Asp Gln
        35

<210> SEQ ID NO 24
<211> LENGTH: 45
<212> TYPE: PRT
<213> ORGANISM: Human immunodeficiency virus type 1

<400> SEQUENCE: 24

Ser Gly Ile Val Gln Gln Gln Ser Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Val Leu Ala Val Glu Arg Tyr Leu Gln Asp Gln
        35                  40                  45

<210> SEQ ID NO 25
<211> LENGTH: 36
<212> TYPE: PRT
<213> ORGANISM: Human immunodeficiency virus type 1

<400> SEQUENCE: 25

Ser Gly Ile Val Gln Gln Gln Ser Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Val Leu
        35

<210> SEQ ID NO 26
<211> LENGTH: 38
<212> TYPE: PRT
<213> ORGANISM: Human immunodeficiency virus type 1

<400> SEQUENCE: 26

Ser Asn Leu Leu Arg Ala Ile Glu Ala Gln Gln His Leu Leu Gln Leu

```
                1               5                    10                   15
Thr Val Trp Gly Ile Lys Gln Leu Gln Ala Arg Val Leu Ala Val Glu
                    20                  25                  30

Arg Tyr Leu Gln Asp Gln
            35

<210> SEQ ID NO 27
<211> LENGTH: 45
<212> TYPE: PRT
<213> ORGANISM: Human immunodeficiency virus type 1

<400> SEQUENCE: 27

Ser Gly Ile Val Gln Gln Gln Ser Asn Leu Leu Arg Ala Ile Glu Ala
1               5                   10                  15

Gln Gln His Leu Leu Gln Leu Thr Val Trp Gly Ile Lys Gln Leu Gln
                20                  25                  30

Ala Arg Val Leu Ala Leu Glu Arg Tyr Leu Arg Asp Gln
            35                  40                  45

<210> SEQ ID NO 28
<211> LENGTH: 38
<212> TYPE: PRT
<213> ORGANISM: Human immunodeficiency virus type 1

<400> SEQUENCE: 28

Ser Asn Leu Leu Arg Ala Ile Glu Ala Gln Gln His Leu Leu Gln Leu
1               5                   10                  15

Thr Val Trp Gly Ile Lys Gln Leu Gln Ala Arg Val Leu Ala Leu Glu
                20                  25                  30

Arg Tyr Leu Arg Asp Gln
            35

<210> SEQ ID NO 29
<211> LENGTH: 45
<212> TYPE: PRT
<213> ORGANISM: Human immunodeficiency virus type 1

<400> SEQUENCE: 29

Ser Gly Ile Val Gln Gln Gln Ser Asn Leu Leu Arg Ala Ile Gln Ala
1               5                   10                  15

Gln Gln His Met Leu Gln Leu Thr Val Trp Gly Val Lys Gln Leu Gln
                20                  25                  30

Ala Arg Val Leu Ala Val Glu Arg Tyr Leu Lys Asp Gln
            35                  40                  45

<210> SEQ ID NO 30
<211> LENGTH: 36
<212> TYPE: PRT
<213> ORGANISM: Human immunodeficiency virus type 1

<400> SEQUENCE: 30

Ser Gly Ile Val Gln Gln Gln Ser Asn Leu Leu Arg Ala Ile Gln Ala
1               5                   10                  15

Gln Gln His Met Leu Gln Leu Thr Val Trp Gly Val Lys Gln Leu Gln
                20                  25                  30

Ala Arg Val Leu
            35

<210> SEQ ID NO 31
<211> LENGTH: 38
```

```
<212> TYPE: PRT
<213> ORGANISM: Human immunodeficiency virus type 1

<400> SEQUENCE: 31

Ser Asn Leu Leu Arg Ala Ile Gln Ala Gln Gln His Met Leu Gln Leu
1               5                   10                  15

Thr Val Trp Gly Val Lys Gln Leu Gln Ala Arg Val Leu Ala Val Glu
            20                  25                  30

Arg Tyr Leu Lys Asp Gln
        35

<210> SEQ ID NO 32
<211> LENGTH: 45
<212> TYPE: PRT
<213> ORGANISM: Human immunodeficiency virus type 1

<400> SEQUENCE: 32

Ser Gly Ile Val Gln Gln Gln Ser Asn Leu Leu Lys Ala Ile Glu Ala
1               5                   10                  15

Gln Gln His Leu Leu Lys Leu Thr Val Trp Gly Ile Lys Gln Leu Gln
            20                  25                  30

Ala Arg Val Leu Ala Val Glu Arg Tyr Leu Lys Asp Gln
        35                  40                  45

<210> SEQ ID NO 33
<211> LENGTH: 36
<212> TYPE: PRT
<213> ORGANISM: Human immunodeficiency virus type 1

<400> SEQUENCE: 33

Ser Gly Ile Val Gln Gln Gln Ser Asn Leu Leu Lys Ala Ile Glu Ala
1               5                   10                  15

Gln Gln His Leu Leu Lys Leu Thr Val Trp Gly Ile Lys Gln Leu Gln
            20                  25                  30

Ala Arg Val Leu
        35

<210> SEQ ID NO 34
<211> LENGTH: 38
<212> TYPE: PRT
<213> ORGANISM: Human immunodeficiency virus type 1

<400> SEQUENCE: 34

Ser Asn Leu Leu Lys Ala Ile Glu Ala Gln Gln His Leu Leu Lys Leu
1               5                   10                  15

Thr Val Trp Gly Ile Lys Gln Leu Gln Ala Arg Val Leu Ala Val Glu
            20                  25                  30

Arg Tyr Leu Lys Asp Gln
        35

<210> SEQ ID NO 35
<211> LENGTH: 45
<212> TYPE: PRT
<213> ORGANISM: Human immunodeficiency virus type 1

<400> SEQUENCE: 35

Ser Gly Ile Val Gln Gln Gln Asn Ile Leu Leu Arg Ala Ile Glu Ala
1               5                   10                  15

Gln Gln His Leu Leu Gln Leu Ser Ile Trp Gly Ile Lys Gln Leu Gln
            20                  25                  30
```

-continued

```
Ala Lys Val Leu Ala Ile Glu Arg Tyr Leu Arg Asp Gln
        35                  40                  45

<210> SEQ ID NO 36
<211> LENGTH: 36
<212> TYPE: PRT
<213> ORGANISM: Human immunodeficiency virus type 1

<400> SEQUENCE: 36

Ser Gly Ile Val Gln Gln Gln Asn Ile Leu Arg Ala Ile Glu Ala
1               5                   10                  15

Gln Gln His Leu Leu Gln Leu Ser Ile Trp Gly Ile Lys Gln Leu Gln
            20                  25                  30

Ala Lys Val Leu
        35

<210> SEQ ID NO 37
<211> LENGTH: 38
<212> TYPE: PRT
<213> ORGANISM: Human immunodeficiency virus type 1

<400> SEQUENCE: 37

Asn Ile Leu Leu Arg Ala Ile Glu Ala Gln Gln His Leu Leu Gln Leu
1               5                   10                  15

Ser Ile Trp Gly Ile Lys Gln Leu Gln Ala Lys Val Leu Ala Ile Glu
            20                  25                  30

Arg Tyr Leu Arg Asp Gln
        35

<210> SEQ ID NO 38
<211> LENGTH: 45
<212> TYPE: PRT
<213> ORGANISM: Human immunodeficiency virus type 1
<220> FEATURE:
<221> NAME/KEY: UNSURE
<222> LOCATION: (25)..(25)
<223> OTHER INFORMATION: May be any amino acid

<400> SEQUENCE: 38

Lys Gly Ile Val Gln Gln Gln Asp Asn Leu Leu Arg Ala Ile Gln Ala
1               5                   10                  15

Gln Gln Gln Leu Leu Arg Leu Ser Xaa Trp Gly Ile Arg Gln Leu Arg
            20                  25                  30

Ala Arg Leu Leu Ala Leu Glu Thr Leu Leu Gln Asn Gln
        35                  40                  45

<210> SEQ ID NO 39
<211> LENGTH: 35
<212> TYPE: PRT
<213> ORGANISM: Human immunodeficiency virus type 1
<220> FEATURE:
<221> NAME/KEY: UNSURE
<222> LOCATION: (25)..(25)
<223> OTHER INFORMATION: May be any amino acid

<400> SEQUENCE: 39

Lys Gly Ile Val Gln Gln Gln Asp Asn Leu Leu Arg Ala Ile Gln Ala
1               5                   10                  15

Gln Gln Gln Leu Leu Arg Leu Ser Xaa Trp Gly Ile Arg Gln Leu Arg
            20                  25                  30

Ala Arg Leu
        35
```

-continued

```
<210> SEQ ID NO 40
<211> LENGTH: 38
<212> TYPE: PRT
<213> ORGANISM: Human immunodeficiency virus type 1
<220> FEATURE:
<221> NAME/KEY: UNSURE
<222> LOCATION: (18)..(18)
<223> OTHER INFORMATION: May be any amino acid

<400> SEQUENCE: 40

Asp Asn Leu Leu Arg Ala Ile Gln Ala Gln Gln Gln Leu Leu Arg Leu
1               5                   10                  15

Ser Xaa Trp Gly Ile Arg Gln Leu Arg Ala Arg Leu Leu Ala Leu Glu
            20                  25                  30

Thr Leu Leu Gln Asn Gln
            35

<210> SEQ ID NO 41
<211> LENGTH: 46
<212> TYPE: PRT
<213> ORGANISM: Human immunodeficiency virus type 1

<400> SEQUENCE: 41

Trp Met Glu Trp Asp Arg Glu Ile Asn Asn Tyr Thr Ser Leu Ile His
1               5                   10                  15

Ser Leu Ile Glu Glu Ser Gln Asn Gln Glu Lys Asn Glu Gln Glu
            20                  25                  30

Leu Leu Glu Leu Asp Lys Trp Ala Ser Leu Trp Asn Trp Phe
        35                  40                  45

<210> SEQ ID NO 42
<211> LENGTH: 46
<212> TYPE: PRT
<213> ORGANISM: Human immunodeficiency virus type 1

<400> SEQUENCE: 42

Trp Met Glu Trp Glu Arg Glu Ile Glu Asn Tyr Thr Gly Leu Ile Tyr
1               5                   10                  15

Thr Leu Ile Glu Glu Ser Gln Asn Gln Gln Glu Lys Asn Glu Gln Asp
            20                  25                  30

Leu Leu Ala Leu Asp Lys Trp Ala Ser Leu Trp Asn Trp Phe
        35                  40                  45

<210> SEQ ID NO 43
<211> LENGTH: 34
<212> TYPE: PRT
<213> ORGANISM: Human immunodeficiency virus type 1

<400> SEQUENCE: 43

Trp Met Glu Trp Glu Arg Glu Ile Glu Asn Tyr Thr Gly Leu Ile Tyr
1               5                   10                  15

Thr Leu Ile Glu Glu Ser Gln Asn Gln Gln Glu Lys Asn Glu Gln Asp
            20                  25                  30
Leu Leu

<210> SEQ ID NO 44
<211> LENGTH: 36
<212> TYPE: PRT
<213> ORGANISM: Human immunodeficiency virus type 1

<400> SEQUENCE: 44

Tyr Thr Gly Leu Ile Tyr Thr Leu Ile Glu Glu Ser Gln Asn Gln Gln
```

-continued

```
                1               5                  10                 15
Glu Lys Asn Glu Gln Asp Leu Leu Ala Leu Asp Lys Trp Ala Ser Leu
            20                  25                 30

Trp Asn Trp Phe
            35
```

<210> SEQ ID NO 45
<211> LENGTH: 46
<212> TYPE: PRT
<213> ORGANISM: Human immunodeficiency virus type 1

<400> SEQUENCE: 45

```
Trp Met Glu Trp Glu Arg Glu Ile Asp Asn Tyr Thr Ser Glu Ile Tyr
1               5                   10                  15

Thr Leu Ile Glu Glu Ser Gln Asn Gln Gln Glu Lys Asn Glu Gln Glu
            20                  25                  30

Leu Leu Glu Leu Asp Lys Trp Ala Ser Leu Trp Asn Trp Phe
            35                  40                  45
```

<210> SEQ ID NO 46
<211> LENGTH: 34
<212> TYPE: PRT
<213> ORGANISM: Human immunodeficiency virus type 1

<400> SEQUENCE: 46

```
Trp Met Glu Trp Glu Arg Glu Ile Asp Asn Tyr Thr Ser Glu Ile Tyr
1               5                   10                  15

Thr Leu Ile Glu Glu Ser Gln Asn Gln Gln Glu Lys Asn Glu Gln Glu
            20                  25                  30

Leu Leu
```

<210> SEQ ID NO 47
<211> LENGTH: 36
<212> TYPE: PRT
<213> ORGANISM: Human immunodeficiency virus type 1

<400> SEQUENCE: 47

```
Tyr Thr Ser Glu Ile Tyr Thr Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
            35
```

<210> SEQ ID NO 48
<211> LENGTH: 46
<212> TYPE: PRT
<213> ORGANISM: Human immunodeficiency virus type 1

<400> SEQUENCE: 48

```
Trp Met Glu Trp Glu Arg Glu Ile Asp Asn Tyr Thr Asp Tyr Ile Tyr
1               5                   10                  15

Asp Leu Leu Glu Lys Ser Gln Thr Gln Gln Glu Lys Asn Glu Lys Glu
            20                  25                  30

Leu Leu Glu Leu Asp Lys Trp Ala Ser Leu Trp Asn Trp Phe
            35                  40                  45
```

<210> SEQ ID NO 49
<211> LENGTH: 34
<212> TYPE: PRT

<213> ORGANISM: Human immunodeficiency virus type 1

<400> SEQUENCE: 49

Trp Met Glu Trp Glu Arg Glu Ile Asp Asn Tyr Thr Asp Tyr Ile Tyr
1               5                   10                  15

Asp Leu Leu Glu Lys Ser Gln Thr Gln Gln Glu Lys Asn Glu Lys Glu
            20                  25                  30

Leu Leu

<210> SEQ ID NO 50
<211> LENGTH: 36
<212> TYPE: PRT
<213> ORGANISM: Human immunodeficiency virus type 1

<400> SEQUENCE: 50

Tyr Thr Asp Tyr Ile Tyr Asp Leu Leu Glu Lys Ser Gln Thr Gln Gln
1               5                   10                  15

Glu Lys Asn Glu Lys Glu Leu Leu Glu Leu Asp Lys Trp Ala Ser Leu
            20                  25                  30

Trp Asn Trp Phe
        35

<210> SEQ ID NO 51
<211> LENGTH: 46
<212> TYPE: PRT
<213> ORGANISM: Human immunodeficiency virus type 1

<400> SEQUENCE: 51

Trp Ile Gln Trp Asp Arg Glu Ile Ser Asn Tyr Thr Gly Ile Ile Tyr
1               5                   10                  15

Arg Leu Leu Glu Glu Ser Gln Asn Gln Gln Glu Asn Asn Glu Lys Asp
            20                  25                  30

Leu Leu Ala Leu Asp Lys Trp Gln Asn Leu Trp Ser Trp Phe
        35                  40                  45

<210> SEQ ID NO 52
<211> LENGTH: 34
<212> TYPE: PRT
<213> ORGANISM: Human immunodeficiency virus type 1

<400> SEQUENCE: 52

Trp Ile Gln Trp Asp Arg Glu Ile Ser Asn Tyr Thr Gly Ile Ile Tyr
1               5                   10                  15

Arg Leu Leu Glu Glu Ser Gln Asn Gln Gln Glu Asn Asn Glu Lys Asp
            20                  25                  30

Leu Leu

<210> SEQ ID NO 53
<211> LENGTH: 36
<212> TYPE: PRT
<213> ORGANISM: Human immunodeficiency virus type 1

<400> SEQUENCE: 53

Tyr Thr Gly Ile Ile Tyr Arg Leu Leu Glu Glu Ser Gln Asn Gln Gln
1               5                   10                  15

Glu Asn Asn Glu Lys Asp Leu Leu Ala Leu Asp Lys Trp Gln Asn Leu
            20                  25                  30

Trp Ser Trp Phe
        35

```
<210> SEQ ID NO 54
<211> LENGTH: 46
<212> TYPE: PRT
<213> ORGANISM: Human immunodeficiency virus type 1

<400> SEQUENCE: 54

Trp Met Glu Trp Glu Arg Glu Ile Ser Asn Tyr Thr Gly Leu Ile Tyr
1               5                   10                  15

Asp Leu Ile Glu Glu Ser Gln Ile Gln Gln Glu Lys Asn Glu Lys Asp
            20                  25                  30

Leu Leu Glu Leu Asp Lys Trp Ala Ser Leu Trp Asn Trp Phe
        35                  40                  45

<210> SEQ ID NO 55
<211> LENGTH: 34
<212> TYPE: PRT
<213> ORGANISM: Human immunodeficiency virus type 1

<400> SEQUENCE: 55

Trp Met Glu Trp Glu Arg Glu Ile Ser Asn Tyr Thr Gly Leu Ile Tyr
1               5                   10                  15

Asp Leu Ile Glu Glu Ser Gln Ile Gln Gln Glu Lys Asn Glu Lys Asp
            20                  25                  30

Leu Leu

<210> SEQ ID NO 56
<211> LENGTH: 36
<212> TYPE: PRT
<213> ORGANISM: Human immunodeficiency virus type 1

<400> SEQUENCE: 56

Tyr Thr Gly Leu Ile Tyr Asp Leu Ile Glu Glu Ser Gln Ile Gln Gln
1               5                   10                  15

Glu Lys Asn Glu Lys Asp Leu Leu Glu Leu Asp Lys Trp Ala Ser Leu
            20                  25                  30

Trp Asn Trp Phe
        35

<210> SEQ ID NO 57
<211> LENGTH: 46
<212> TYPE: PRT
<213> ORGANISM: Human immunodeficiency virus type 1

<400> SEQUENCE: 57

Trp Met Glu Trp Gln Lys Glu Ile Ser Asn Tyr Ser Asn Glu Val Tyr
1               5                   10                  15

Arg Leu Ile Glu Lys Ser Gln Asn Gln Gln Glu Lys Asn Glu Gln Gly
            20                  25                  30

Leu Leu Ala Leu Asp Lys Trp Ala Ser Leu Trp Asn Trp Phe
        35                  40                  45

<210> SEQ ID NO 58
<211> LENGTH: 34
<212> TYPE: PRT
<213> ORGANISM: Human immunodeficiency virus type 1

<400> SEQUENCE: 58

Trp Met Glu Trp Gln Lys Glu Ile Ser Asn Tyr Ser Asn Glu Val Tyr
1               5                   10                  15

Arg Leu Ile Glu Lys Ser Gln Asn Gln Gln Glu Lys Asn Glu Gln Gly
```

Leu Leu

<210> SEQ ID NO 59
<211> LENGTH: 36
<212> TYPE: PRT
<213> ORGANISM: Human immunodeficiency virus type 1

<400> SEQUENCE: 59

Tyr Ser Asn Glu Val Tyr Arg Leu Ile Glu Lys Ser Gln Asn Gln Gln
1               5                   10                  15

Glu Lys Asn Glu Gln Gly Leu Leu Ala Leu Asp Lys Trp Ala Ser Leu
            20                  25                  30

Trp Asn Trp Phe
        35

<210> SEQ ID NO 60
<211> LENGTH: 46
<212> TYPE: PRT
<213> ORGANISM: Human immunodeficiency virus type 1

<400> SEQUENCE: 60

Trp Ile Gln Trp Asp Arg Glu Ile Ser Asn Tyr Thr Gln Gln Ile Tyr
1               5                   10                  15

Ser Leu Ile Glu Glu Ser Gln Asn Gln Gln Glu Lys Asn Glu Gln Asp
            20                  25                  30

Leu Leu Ala Leu Asp Asn Trp Ala Ser Leu Trp Thr Trp Phe
        35                  40                  45

<210> SEQ ID NO 61
<211> LENGTH: 34
<212> TYPE: PRT
<213> ORGANISM: Human immunodeficiency virus type 1

<400> SEQUENCE: 61

Trp Ile Gln Trp Asp Arg Glu Ile Ser Asn Tyr Thr Gln Gln Ile Tyr
1               5                   10                  15

Ser Leu Ile Glu Glu Ser Gln Asn Gln Gln Glu Lys Asn Glu Gln Asp
            20                  25                  30

Leu Leu

<210> SEQ ID NO 62
<211> LENGTH: 36
<212> TYPE: PRT
<213> ORGANISM: Human immunodeficiency virus type 1

<400> SEQUENCE: 62

Tyr Thr Gln Gln Ile Tyr Ser Leu Ile Glu Glu Ser Gln Asn Gln Gln
1               5                   10                  15

Glu Lys Asn Glu Gln Asp Leu Leu Ala Leu Asp Asn Trp Ala Ser Leu
            20                  25                  30

Trp Thr Trp Phe
        35

<210> SEQ ID NO 63
<211> LENGTH: 46
<212> TYPE: PRT
<213> ORGANISM: Human immunodeficiency virus type 1

<400> SEQUENCE: 63

```
Trp Met Glu Trp Asp Arg Gln Ile Asp Asn Tyr Thr Glu Val Ile Tyr
1               5                   10                  15

Arg Leu Leu Glu Leu Ser Gln Thr Gln Gln Glu Gln Asn Glu Gln Asp
                20                  25                  30

Leu Leu Ala Leu Asp Lys Trp Asp Ser Leu Trp Asn Trp Phe
                35                  40                  45

<210> SEQ ID NO 64
<211> LENGTH: 34
<212> TYPE: PRT
<213> ORGANISM: Human immunodeficiency virus type 1

<400> SEQUENCE: 64

Trp Met Glu Trp Asp Arg Gln Ile Asp Asn Tyr Thr Glu Val Ile Tyr
1               5                   10                  15

Arg Leu Leu Glu Leu Ser Gln Thr Gln Gln Glu Gln Asn Glu Gln Asp
                20                  25                  30

Leu Leu

<210> SEQ ID NO 65
<211> LENGTH: 36
<212> TYPE: PRT
<213> ORGANISM: Human immunodeficiency virus type 1

<400> SEQUENCE: 65

Tyr Thr Glu Val Ile Tyr Arg Leu Leu Glu Leu Ser Gln Thr Gln Gln
1               5                   10                  15

Glu Gln Asn Glu Gln Asp Leu Leu Ala Leu Asp Lys Trp Asp Ser Leu
                20                  25                  30

Trp Asn Trp Phe
                35

<210> SEQ ID NO 66
<211> LENGTH: 47
<212> TYPE: PRT
<213> ORGANISM: Human immunodeficiency virus type 1

<400> SEQUENCE: 66

Trp Ile Gln Trp Glu Arg Glu Ile Asn Asn Tyr Thr Gly Ile Ile Tyr
1               5                   10                  15

Ser Leu Ile Glu Glu Ala Gln Asn Gln Gln Glu Asn Asn Glu Lys Asp
                20                  25                  30

Leu Leu Ala Leu Asp Lys Trp Thr Asn Leu Trp Asn Trp Phe Asn
                35                  40                  45

<210> SEQ ID NO 67
<211> LENGTH: 34
<212> TYPE: PRT
<213> ORGANISM: Human immunodeficiency virus type 1

<400> SEQUENCE: 67

Trp Ile Gln Trp Glu Arg Glu Ile Asn Asn Tyr Thr Gly Ile Ile Tyr
1               5                   10                  15

Ser Leu Ile Glu Glu Ala Gln Asn Gln Gln Glu Asn Asn Glu Lys Asp
                20                  25                  30

Leu Leu

<210> SEQ ID NO 68
<211> LENGTH: 37
<212> TYPE: PRT
```

<213> ORGANISM: Human immunodeficiency virus type 1

<400> SEQUENCE: 68

Tyr Thr Gly Ile Ile Tyr Ser Leu Ile Glu Glu Ala Gln Asn Gln Gln
1               5                   10                  15

Glu Asn Asn Glu Lys Asp Leu Leu Ala Leu Asp Lys Trp Thr Asn Leu
            20                  25                  30

Trp Asn Trp Phe Asn
            35

<210> SEQ ID NO 69
<211> LENGTH: 46
<212> TYPE: PRT
<213> ORGANISM: Human immunodeficiency virus type 1

<400> SEQUENCE: 69

Trp Gln Gln Trp Asp Glu Lys Val Arg Asn Tyr Ser Gly Val Ile Phe
1               5                   10                  15

Gly Leu Ile Glu Gln Ala Gln Glu Gln Gln Asn Thr Asn Glu Lys Ser
            20                  25                  30

Leu Leu Glu Leu Asp Gln Trp Asp Ser Leu Trp Ser Trp Phe
        35                  40                  45

<210> SEQ ID NO 70
<211> LENGTH: 34
<212> TYPE: PRT
<213> ORGANISM: Human immunodeficiency virus type 1

<400> SEQUENCE: 70

Trp Gln Gln Trp Asp Glu Lys Val Arg Asn Tyr Ser Gly Val Ile Phe
1               5                   10                  15

Gly Leu Ile Glu Gln Ala Gln Glu Gln Gln Asn Thr Asn Glu Lys Ser
            20                  25                  30

Leu Leu

<210> SEQ ID NO 71
<211> LENGTH: 36
<212> TYPE: PRT
<213> ORGANISM: Human immunodeficiency virus type 1

<400> SEQUENCE: 71

Tyr Ser Gly Val Ile Phe Gly Leu Ile Glu Gln Ala Gln Glu Gln Gln
1               5                   10                  15

Asn Thr Asn Glu Lys Ser Leu Leu Glu Leu Asp Gln Trp Asp Ser Leu
            20                  25                  30

Trp Ser Trp Phe
            35

<210> SEQ ID NO 72
<211> LENGTH: 46
<212> TYPE: PRT
<213> ORGANISM: Human immunodeficiency virus type 1

<400> SEQUENCE: 72

Trp Gln Glu Trp Asp Arg Gln Ile Ser Asn Ile Ser Ser Thr Ile Tyr
1               5                   10                  15

Glu Glu Ile Gln Lys Ala Gln Val Gln Gln Glu Gln Asn Glu Lys Lys
            20                  25                  30

Leu Leu Glu Leu Asp Glu Trp Ala Ser Ile Trp Asn Trp Leu
        35                  40                  45

-continued

<210> SEQ ID NO 73
<211> LENGTH: 34
<212> TYPE: PRT
<213> ORGANISM: Human immunodeficiency virus type 1

<400> SEQUENCE: 73

```
Trp Gln Glu Trp Asp Arg Gln Ile Ser Asn Ile Ser Ser Thr Ile Tyr
1               5                   10                  15

Glu Glu Ile Gln Lys Ala Gln Val Gln Gln Glu Gln Asn Glu Lys Lys
            20                  25                  30

Leu Leu
```

<210> SEQ ID NO 74
<211> LENGTH: 36
<212> TYPE: PRT
<213> ORGANISM: Human immunodeficiency virus type 1

<400> SEQUENCE: 74

```
Ile Ser Ser Thr Ile Tyr Glu Glu Ile Gln Lys Ala Gln Val Gln Gln
1               5                   10                  15

Glu Gln Asn Glu Lys Lys Leu Leu Glu Leu Asp Glu Trp Ala Ser Ile
            20                  25                  30

Trp Asn Trp Leu
        35
```

<210> SEQ ID NO 75
<211> LENGTH: 53
<212> TYPE: PRT
<213> ORGANISM: respiratory syncytial virus

<400> SEQUENCE: 75

```
Gly Glu Pro Ile Ile Asn Phe Tyr Asp Pro Leu Val Phe Pro Ser Asp
1               5                   10                  15

Glu Phe Asp Ala Ser Ile Ser Gln Val His Glu Lys Ile Asn Gln Ser
            20                  25                  30

Leu Ala Phe Ile Arg Lys Ser Asp Glu Leu Leu His Asn Val Asn Ala
        35                  40                  45

Gly Lys Ser Thr Thr
    50
```

<210> SEQ ID NO 76
<211> LENGTH: 56
<212> TYPE: PRT
<213> ORGANISM: Human parainfluenza virus 3

<400> SEQUENCE: 76

```
Tyr Thr Pro Asn Asp Ile Thr Leu Asn Asn Ser Val Ala Leu Asp Pro
1               5                   10                  15

Ile Asp Ile Ser Ile Glu Leu Asn Lys Ala Lys Ser Asp Leu Glu Glu
            20                  25                  30

Ser Lys Glu Trp Ile Arg Arg Ser Asn Gln Lys Leu Asp Ser Ile Gly
        35                  40                  45

Asn Trp His Gln Ser Ser Thr Thr
    50                  55
```

<210> SEQ ID NO 77
<211> LENGTH: 50
<212> TYPE: PRT
<213> ORGANISM: Measles virus -continued

```
<400> SEQUENCE: 77

Pro Asp Ala Val Tyr Leu His Arg Ile Asp Leu Gly Pro Pro Ile Ser
1               5                   10                  15

Leu Glu Arg Leu Asp Val Gly Thr Asn Leu Asn Ala Ile Ala Lys Leu
            20                  25                  30

Glu Asp Ala Lys Glu Leu Leu Glu Ser Ser Asp Gln Ile Leu Arg Ser
        35                  40                  45

Met Lys
    50
```

ASSAY FOR DETECTION OF VIRAL FUSION INHIBITORS

STATEMENT AS TO RIGHTS TO INVENTIONS MADE UNDER FEDERALLY-SPONSORED RESEARCH AND DEVELOPMENT

This application claims the benefit, under 35 U.S.C. §119(e), of the earlier filing date of U.S. Provisional Application No. 60/235,901, filed on Sep. 28, 2000 and of the earlier filing data of U.S. Provisional Application No. 60/181,543 filed on Feb. 10, 2000. The entirtey of both applications is fully incorporated by reference herein.

Part of the work performed during development of this invention utilized U.S. Government funds. The U.S. Government has certain rights in this invention.

BACKGROUND OF THE INVENTION

1. Field of the Invention

The invention is directed to methods for identifying compounds that inhibit or prevent infection of cells by enveloped viruses such as HIV-1, and the compounds discovered by such methods. The invention also includes using these methods as diagnostic assays to detect antibodies in virus-infected individuals that inhibit the viral entry processes.

2. Related Art

The HIV-1 envelope glycoprotein is a 160 kDa glycoprotein that is cleaved to form the transmembrane (TM) subunit, gp41, which is non-covalently attached to the surface (SU) subunit, gp120 (Allan J. S., et al., *Science* 228:1091–1094 (1985); Veronese F. D., et al., *Science* 229:1402–1405 (1985)). Recent efforts have led to a clearer understanding of the structural components of the HIV-1 envelope system. Such efforts include crystallographic analysis of significant portions of both gp120 and gp41 (Kwong, P. D., et al., *Nature (London)* 393:648–659 (1998); Chan, D. C., et al., *Cell* 89:263–273 (1997); Weissenhorn, W., et al., *Nature* 387:426–430 (1997)).

The surface subunit has been characterized as part of a multi-component complex consisting of the SU protein (the gp120 core absent the variable loops) bound to a soluble form of the cellular receptor CD4 (N-terminal domains 1 and 2 containing amino acid residues 1–181) and an antigen binding fragment of a neutralizing antibody (amino acid residues 1–213 of the light chain and 1–229 of the heavy chain of the 17b monoclonal antibody) which blocks chemokine receptor binding (Kwong, P. D., et al., *Nature (London)* 393:648–659 (1998)). Several envelope components believed to exist only in the fusion-active form of gp120 were revealed by the crystallographic analysis including a conserved binding site for the chemokine receptor, a CD4-induced epitope and a cavity-laden CD4-gp120 interface. This supports earlier observations of CD4-induced changes in gp120 conformation.

The gp120/gp41 complex is present as a trimer on the virion surface where it mediates virus attachment and fusion. HIV-1 replication is initiated by the high affinity binding of gp 120 to the cellular receptor CD4 and the expression of this receptor is a primary determinant of HIV-1 cellular tropism in vivo (Dalgleish, A. G., et al., *Nature* 312:763–767 (1984); Lifson, J. D., et al., *Nature* 323:725–728 (1986); Lifson, J. D., et al., *Science* 232:1123–1127 (1986); McDougal, J. S., et al., *Science* 231:382–385 (1986)). The gp120-binding site on CD4 has been localized to the CDR2 region of the N-terminal V1 domain of this four-domain protein (Arthos, J., et al., *Cell* 5:469–481 (1989)). The CD4-binding site on gp120 maps to discontinuous regions of gp120 including the C2, C3 and C4 domains (Olshevsky, U., et al., *Virol* 64:5701–5707 (1990); Kwong, P. D., et al., *Nature (London)* 393:648–659 (1998)). Following attachment to CD4, the virus must interact with a "second" receptor such as a chemokine receptor in order to initiate the fusion process. Recently, researchers have identified the critical role of members of the chemokine receptor family in HIV entry (McDougal J. S., et al., *Science* 231:382–385 (1986); Feng Y., et al., *Science* 272:872–877 (1996); Alkhatib G., et al., *Science* 272:1955–1958 (1996); Doranz B. J., et al., *Cell* 85:1149–1158 (1996); Deng H., et al., *Nature* 381:661–666 (1996); Dragic T., et al., *Nature* 381:667–673 (1996); Choe H., et al., *Cell* 85:1135–1148 (1996); Dimitrov D. S., *Nat. Med.* 2:640–641 (1996); Broder, C. C. and Dimitrov, D. S., *Pathobiology* 64:171–179 (1996)). CCR5 is the chemokine receptor used by macrophage-tropic and many T-cell tropic primary HIV-1 isolates. Most T-cell line-adapted strains use CXCR4, while many T-cell tropic isolates are dual tropic, capable of using both CCR5 and CXCR4.

Binding of gp120 to CD4 and a chemokine receptor initiates a series of conformational changes within the HIV envelope system (Eiden, L. E. and Lifson, J. D., *Immunol. Today* 13:201–206 (1992); Sattentau, Q. J. and Moore J. P., *J. Exp. Med.* 174:407–415 (1991); Allan J. S., et al., *AIDS Res Hum Retroviruses* 8:2011–2020 (1992); Clapham, P. R., et al., *J. Virol.* 66:3531–3537 (1992)). These changes occur in both the surface and transmembrane subunits and result in the formation of envelope structures which are necessary for virus entry. The functions of gp41 and gp120 appear to involve positioning the virus and cell membranes in close proximity thereby facilitating membrane fusion (Bosch M. L., et al., *Science* 244:694–697 (1989); Slepushkin, V. A. et al., *AIDS Res Hum Retroviruses* 8:9–(1992); Freed E. O. et al., *Proc. Natl. Acad. Sci. USA* 87:4650–4654 (1990)).

A good deal of structural information is available with respect to the HIV-1 transmembrane glycoprotein (gp41). This protein contains a number of well-characterized functional regions. See FIG. 3. For example, the N-terminal region consists of a glycine-rich sequence referred to as the fusion peptide which is believed to function by insertion into and disruption of the target cell membrane (Bosch, M. L., et al., *Science* 244:694–697 (1989); Slepushkin, V. A., et al., *AIDS Res. Hum. Retrovirus* 8:9–18 (1992); Freed, E. O., et al., *Proc. Natl. Acad. Sci. USA* 87:4650–4654 (1990); Moore, J. P., et al., "The HIV-cell Fusion Reaction," in *Viral Fusion Mechanism*, Bentz, J., ed., CRC Press, Inc., Boca Raton, Fla.). Another region, characterized by the presence of disulfide linked cysteine residues, has been shown to be immunodominant and is suggested as a contact site for the surface (gp120) and transmembrane glycoproteins (Gnann, J. W., Jr., et al., *J. Virol.* 61:2639–2641 (1987); Norrby, E., et al., *Nature* 329:248–250 (1987); Xu, J. Y., et al., *J. Virol.* 65:4832–4838 (1991)). Other regions in the gp41 ectodomain have been associated with escape from neutralization (Klasse, P. J., et al., *Virology* 196:332–337 (1993); Thali, M., et al., *J. Virol.* 68:674–680 (1994); Stem, T. L., et al., *J. Virol.* 69:1860–1867 (1995)), immunosuppression (Cianciolo, G. J., et al., *Immunol. Lett.* 19:7–13 (1988); Ruegg, C. L., et al., *J. Virol.* 63:3257–3260 (1989)), and target cell binding (Qureshi, N. M., et al., *AIDS* 4:553–558 (1990); Ebenbichler, C. F., et al., *AIDS* 7:489–495 (1993); Henderson, L. A. and Qureshi, M. N., *J. Biol. Chem.* 268:15291–15297 (1993)).

Recent work has increased knowledge of the structural components of the HIV-1 transmembrane glycoprotein, however, the immunogenic nature of gp41 remains poorly understood. It is known that one of two immunodominant regions present in the HIV-1 envelope complex is located in gp41 (Xu, J. Y., et al., *J. Virol.* 65:4832–4838 (1991)). This region (TM residues 597–613) is associated with a strong, albeit non-neutralizing, humoral response in a large number of HIV+ individuals.

Two regions of the ectodomain of gp41 have been shown to be critical to virus entry. Primary sequence analysis predicted that these regions (termed the N-helix (residues 558–595 of the HIV-1$_{LAI}$ sequence) and C-helix (residues 643–678 of the HIV-1$_{LAI}$ sequence)) model the α-helical secondary structure. Experimental efforts stemming from previous structural studies of synthetic peptide mimics established that the sequence analysis predictions were generally correct (Wild, C., et al., *Proc. Natl. Acad. Sci. USA* 89:10537–10541 (1992); Wild, C. T., et al., *Proc. Natl. Acad. Sci. USA* 91:9770–9774 (1994); Gallaher, W. R., et al., *AIDS Res. Hum. Retroviruses* 5:431–440 (1989); Delwart, E. L., et al., *AIDS Res. Hum. Retroviruses* 6:703–704 (1990)). Subsequent structural analysis determined that these regions of the transmembrane protein interact in a specific fashion to form a higher order structure characterized as a trimeric six-helix bundle (Chan, D. C., et al., *Cell* 89:263–273 (1997); Weissenhorn, W., et al., *Nature* 387:426–430 (1997)). This trimeric structure consists of an interior parallel coiled-coil trimeric core (region one, N-helix) which associates with three identical α-helices (region two, C-helix) which pack in an oblique, antiparallel manner into the hydrophobic grooves on the surface of the coiled-coil trimer. This hydrophobic self-assembly domain is believed to constitute the core structure of gp41. See FIGS. 4A and 4B. It has been demonstrated that the N-and C-helical regions of the transmembrane protein are critical to HIV-1 entry. It has been proposed that the association of these two regions to form the six-helix bundle core structure occurs during the transition from a nonfusogenic to a fusion-active form of gp41, and that the formation of this core structure facilitates membrane fusion by bringing the viral and target cell surfaces into close proximity (Chan, D. C. and Kim, P. S., *Cell* 93:681–684 (1998); FIG. 1). If correct, the formation of the six-helix bundle is a key step in virus entry and factors which interfere with its formation could disrupt the entry event. A number of viruses share protein glycoprotein structure similar to N- and C-helical regions of HIV transmembrane protein (Lambert et al., *Proc. Nat. Acad Sci.* 93:2186–2191 (1996). See also, Published PCT Application No. WO96/19495.

All approved drugs for the treatment of human immunodeficiency virus (HIV) infection target either viral reverse transcriptase (RT) or protease activity. Although certain combinations of these drugs have proven highly effective in suppressing virus replication, problems related to complicated dosing regimens and selection for resistant viral isolates necessitate the continued need for the development of additional therapies. To maximize their effect in combination therapy these new drugs should exploit targets other than RT or protease.

Mono- and bi-therapy for human immunodeficiency virus type 1 (HIV-1) infection are only transiently effective mainly due to virus drug resistance. To obtain a sustained benefit from antiviral therapy, current guidelines recommend at least triple-drug combinations, or the so-called highly active antiretroviral therapy (HAART). Despite these advances, there are still problems with the currently available drug regimens. Many of the drugs exhibit severe toxicities or require complicated dosing schedules that reduce compliance and limit efficacy. Resistant strains of HIV usually appear over extended periods of time even on HAART regimens.

For these and other reasons there is a continuing need for the development of additional anti-HIV drugs. Ideally these would target different stages in the viral life cycle, (adding to the armamentarium for combination therapy), exhibit minimal toxicity, and have low manufacturing costs. Small molecule inhibitors of HIV entry could aid significantly in addressing these problems.

It has been proposed that the DP-107 and DP-178 peptides inhibit HIV-1 replication by disrupting formation of the six-helix bundle in a negative-dominant manner (FIG. 2). As prototypes of a new class of HIV inhibitors which block virus entry, these compounds offer additional therapeutic options for use alone or in combination with drugs targeting other steps in virus replication. However, as is often the case with protein-based therapeutics, these peptides are less than ideal drug candidates due to issues of oral bioavailability, in vivo stability and manufacturing costs.

The 2F5 monoclonal antibody, from isolates presenting the gp41 sequence ELDKWAS, is a neutralizing antibody targeting gp41 (Muster, T., et al. *J. Virol.* 67:6642–6647 (1993), and Muster, T., et al., *J. Virol.* 68:4031–4034 (1994)). This antibody maps to the linear amino acid sequence Glu-Leu-Asp-Lys-Trp-Ala (ELDKWA) in the ectodomain of gp41, an epitope which is conserved in 72% of HIV-1 isolates. While this antibody maps to a linear determinant, competition studies suggest that the 2F5 epitope is conformational in nature.

The monoclonal antibody, NC-1 has been shown to bind the six-helix bundle in fusion-active gp41 (Jiang, S., et al., *J. Virol.* 72:10213–10217 (1998)). NC-1 was generated and cloned from a mouse immunized with a mixture of peptides modeling the N- and C-helical domains of gp41. NC-1 binds specifically to both the α-helical (N-helical) core domain and an oligomeric form of gp41. This conformation-dependent reactivity is dramatically reduced by point mutations within the N-terminal coiled-coil region of gp41 which impede formation of the six helix bundle. NC-1 binds to the surfaces of HIV-1-infected cells only in the presence of soluble CD4.

Formaldehyde-fixed, fusion active whole-cell preparations (in transgenic mice) have been used to generate an antisera capable of neutralizing 23 of 24 primary HIV isolates from diverse geographic locations and genetic clades A to E (LaCasse, R. A., et al., *Science* 283:357–362 (1999)). These fusion-competent immunogens may capture the transient envelope-CD4-co-receptor structures that arise during HIV binding and fusion.

SUMMARY OF THE INVENTION

A number of viruses share similar protein/glycoprotein structures which have been implicated in the mechanism of viral fusion and entry into permissive cells. The present invention provides methods of screening for compounds that inhibit viral fusion and/or entry into permissive cells. The screening methods of the invention involve attempting to selectively trigger the formation of one or more critical entry intermediates in cell-surface-expressed viral envelope in the presence of a test compound and probing for the formation or lack of formation of such intermediates. This can be accomplished as described herein.

A specific embodiment of the invention is directed to a method for determining compounds which disrupt formation of critical gp41 structures and conformations necessary for virus entry and therefore block HIV entry. The gp41 six-helix bundle which forms in response to CD4/gp120 binding constitutes one such critical entry structure. Antibodies specific for the six-helix bundle are used to determine the ability of small molecules to block its formation. The method of the present invention can be applied to other viruses where a transmembrane protein or glycoprotein forms structures and complexes that are involved for virus entry, including but not limited to, HIV-2, HTLV-I, HTLV-II, respiratory syncytial virus (RSV), human influenza viruses, parainfluenza virus type 3 (HPIV-3), Newcastle disease virus, feline immuno-deficiency virus (FIV), and measles virus.

The invention is also directed to novel inhibitors identified by these methods, which can be small molecules, peptides, proteins, antibodies and antibody fragments, or derivatives thereof. These inhibitors are suitable for inhibiting or preventing infection by various viruses including HIV-1 and/or the other viruses listed above. These inhibitors can be used to treat humans infected with HIV-1 or the other viruses, or used to prevent infection by HIV-1 or the other viruses. The invention also includes the inhibitors in suitable pharmaceutical compositions.

Compounds that show inhibitory activity in the assays of the current invention may act at any of the several steps leading to, or associated with, the conformational changes in the viral envelope glycoproteins that result in membrane fusion. For example they may inhibit the interaction between the envelope glycoprotein and its receptors which are the triggers that initiate conformation changes in the envelope glycoproteins (e.g. in the case of HIV-1, the interaction between gp120 and CD4 or the CCR5 or CXCR4 chemokine receptors). Alternatively, they may directly inhibit the formation of fusion active structures, e.g. by preventing the association of the alpha helical domains of the transmembrane protein that are part of these structures (e.g. in the case of HIV-1, by blocking the association of the N- and C-helical domains that lead to six helix bundle formation). The assays are also capable of discovering inhibitors of other steps in the process that are as yet not fully elucidated.

Additional assays can be performed to analyze in more detail the mechanism of action of inhibitory compounds discovered in the present invention. The methods for these assays are well know to those skilled in the art. For example, assays to test inhibitors of the HIV-1 gp120 interaction with CD4 or chemokine receptors are described in Dragic, T., et al., *Nature* 381:667–673 (1996) and Donzella, G. A., et al., *Nature Medicine* 4:72–77 (1998). Assays to test inhibitors of HIV-1 gp41 6 helix bundle formation are described in Jiang S. et al., *J. Virol. Methods* 80:85–96 (1999).

This invention also includes the use of the assays described above as diagnostic assays to detect antibodies in virus-infected individuals or virus-infected body fluids or tissues that inhibit entry-relevant conformational changes in one or more viral envelope proteins or glycoproteins. The presence of such antibodies in infected individuals or samples is of prognostic value.

BRIEF DESCRIPTION OF THE FIGURES

FIG. 2A shows co-immunoprecipitation of gp41 by P-18HA following HXB2 envelope activation by binding to soluble and cell expressed CD4 (+/− indicates presence or absence of CD4). FIG. 2B shows the blocking of co-immunoprecipitation of P-18HA binding by an anti-CD4 binding antibody (Q4120, Sigma). FIG. 2C shows the effect of receptor activation (both CD4 and chemokine) on HIV-1 primary, CCR5-dependent isolate envelopes. In each panel, * indicates bands due to IgG heavy chain and ** indicates bands due to shorter fragments of gp41 probably resulting from proteolysis.

FIG. 6A shows results from the lysate immunoprecipitation experiment with polyclonal sera generated against N- and C-helical peptides (individual and mixed) and recombinant gp41. All sera, except that generated by the C-helical peptides, immunoprecipitate HXB2 gp41 in this assay. The presence or absence (+/−) of sCD4 in this experiment did not affect results. FIG. 6B shows the results from the surface immunoprecipitation experiment using this same panel of sera. In this experiment, four sera (N1, N2, C1/N1 mixture and rgp41) exhibited enhanced binding to gp41 following CD4 activation of surface expressed envelope. The bands from the mixed peptide and rgp41 sera are very heavy while the bands form the N-helical peptide sera are much lighter. In each panel * indicates bands due to IgG heavy chain.

DETAILED DESCRIPTION OF THE PREFERRED EMBODIMENTS

Figure 1:
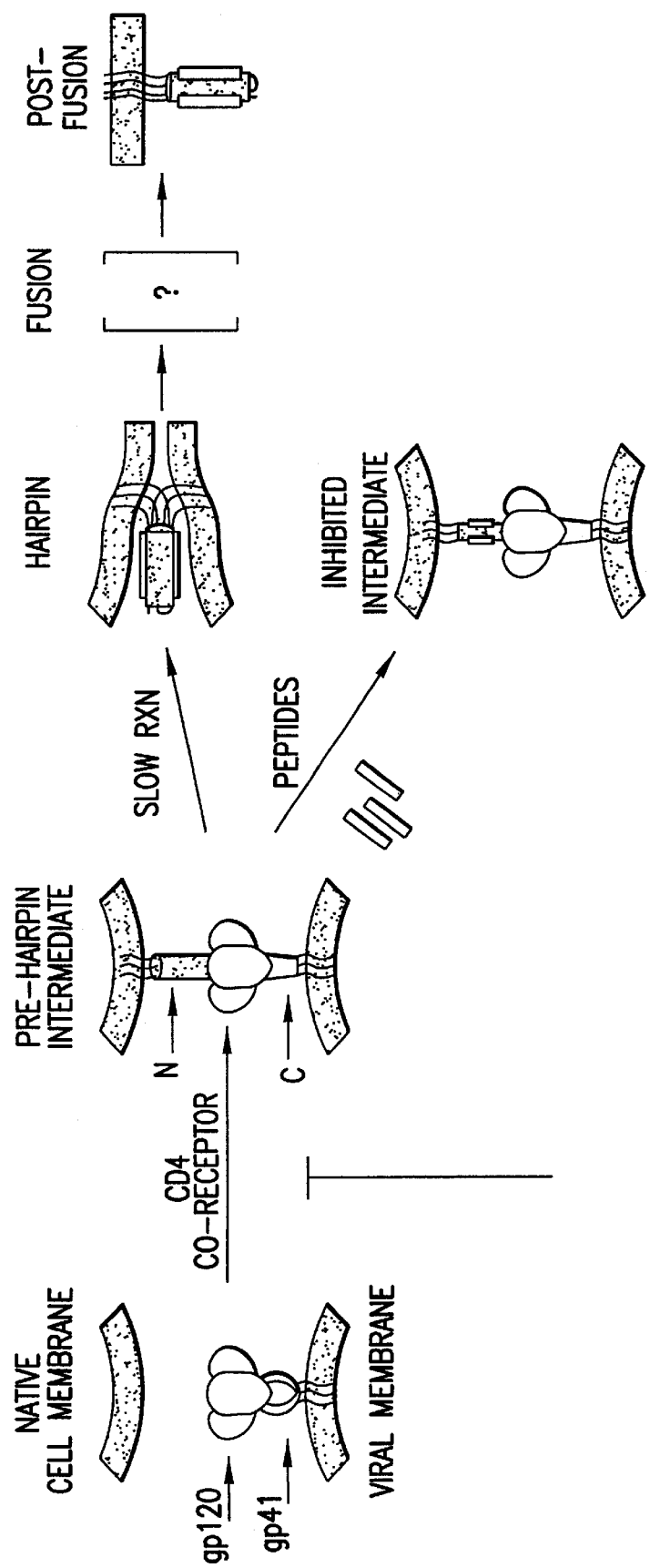
FIG. 1 illustrates the postulated role of gp41 in mediating virus entry. In the native state, the HIV-1 envelope complex exists in a nonfusogenic form. Following CD4 (and in some cases chemokine) binding, a pre-hairpin intermediate forms. At this point, the transmembrane protein, gp41, is in an extended conformation and the N- and C-helical domains have yet to associate. This intermediate proceeds to form the six-helix bundle (hairpin intermediate). Formation of the bundle serves to facilitate virus-target cell fusion by drawing the viral and cellular membranes close together. In the presence of an inhibitor, such as an inhibitory peptide, the pre-hairpin intermediate (extended conformation) is stabilized by the interaction of the peptide with the appropriate complementary region of gp41 to form a "stabilized pre-hairpin intermediate." This stabilization of the pre-hairpin intermediate precludes formation of the six-helix bundle structure, effectively serving as a block to virus entry. The stabilized pre-hairpin intermediate is one form of fusion-active immunogens useful for generating antibodies employed in the methods of the present invention.
Figure 2A:
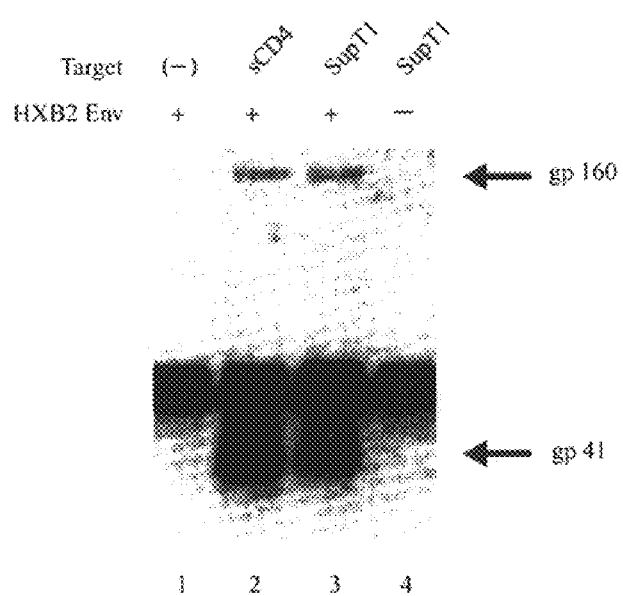
FIGS. 2A–2C illustrate the use of an epitope-tagged peptide, p-18HA, to capture and stabilize a fusion-active form of gp41.
Figure 2B:
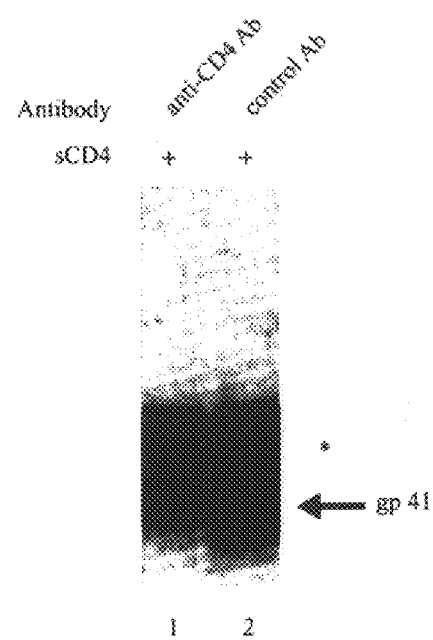
Figure 2C:
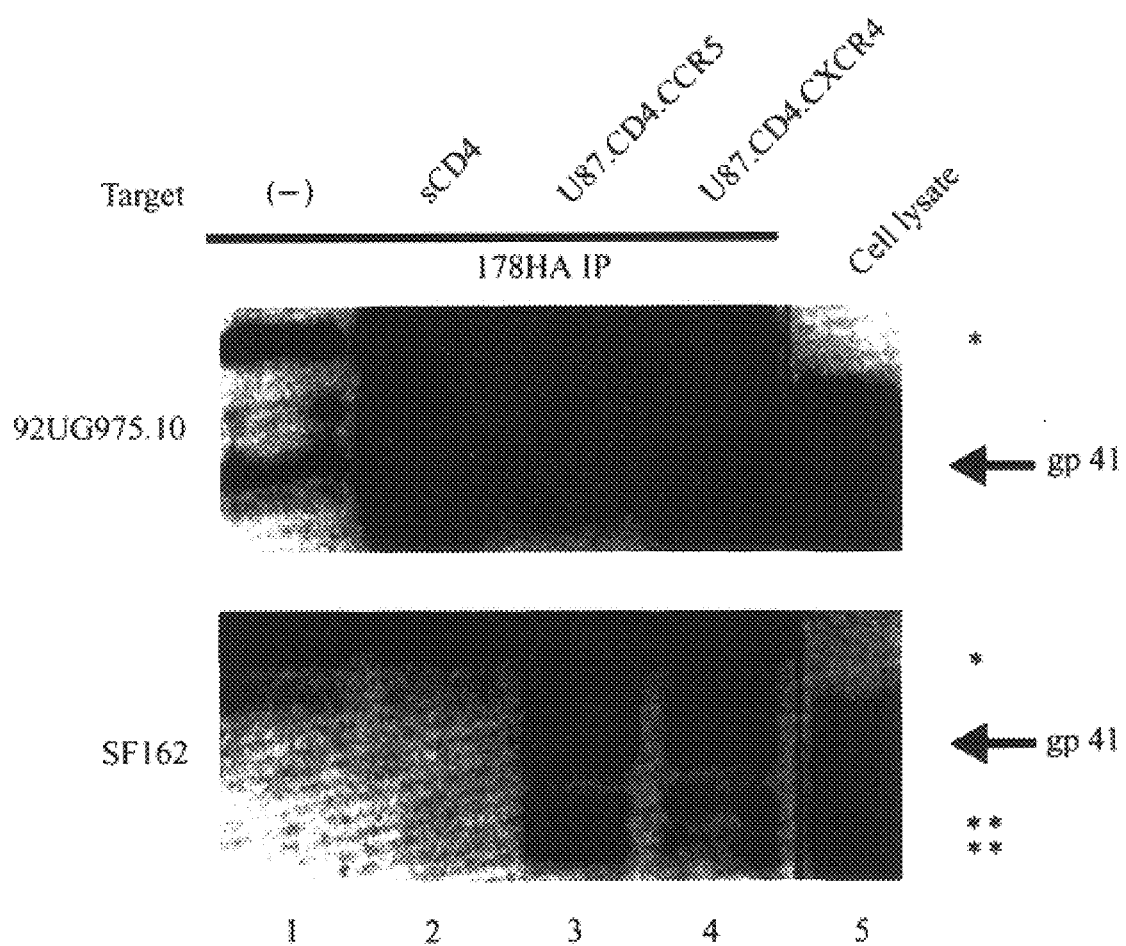
Figure 3:
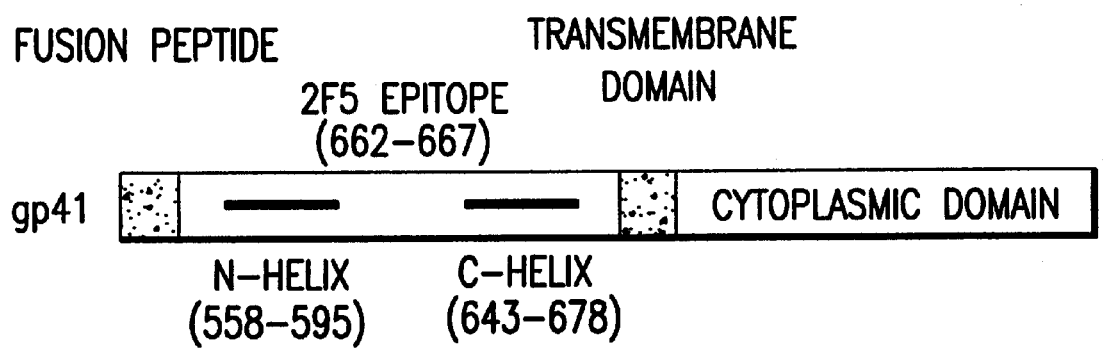
FIG. 3 is a schematic representation of the structural and antigenic regions of HIV-1 gp41. This figure also depicts conformational changes that occurs in these regions when an antibody binds to gp-41.
Figure 4A:
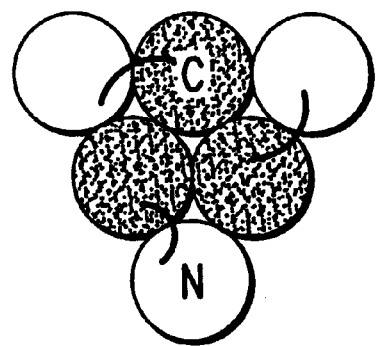
FIGS. 4A and 4B are schematic representations of the interaction of the N- and C-helical domains of gp41 to form the six-helix bundle structure. Both top and side views are shown. The interior of the bundle represents the N-helical coiled-coil. The exterior components represent the C-helical domain.
Figure 4B:
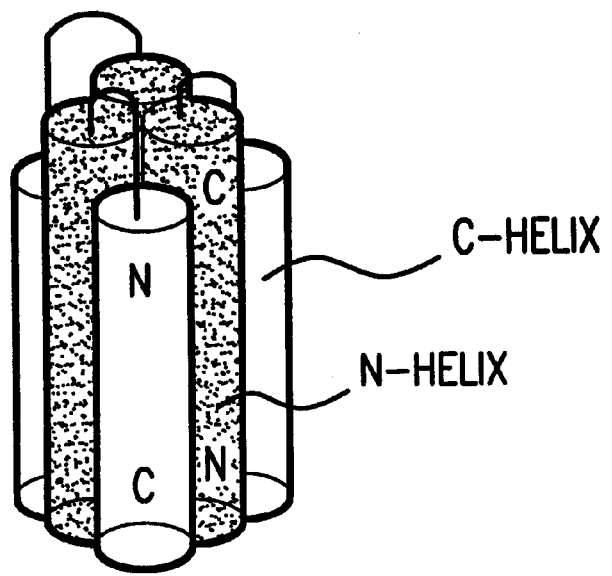
Figure 5:
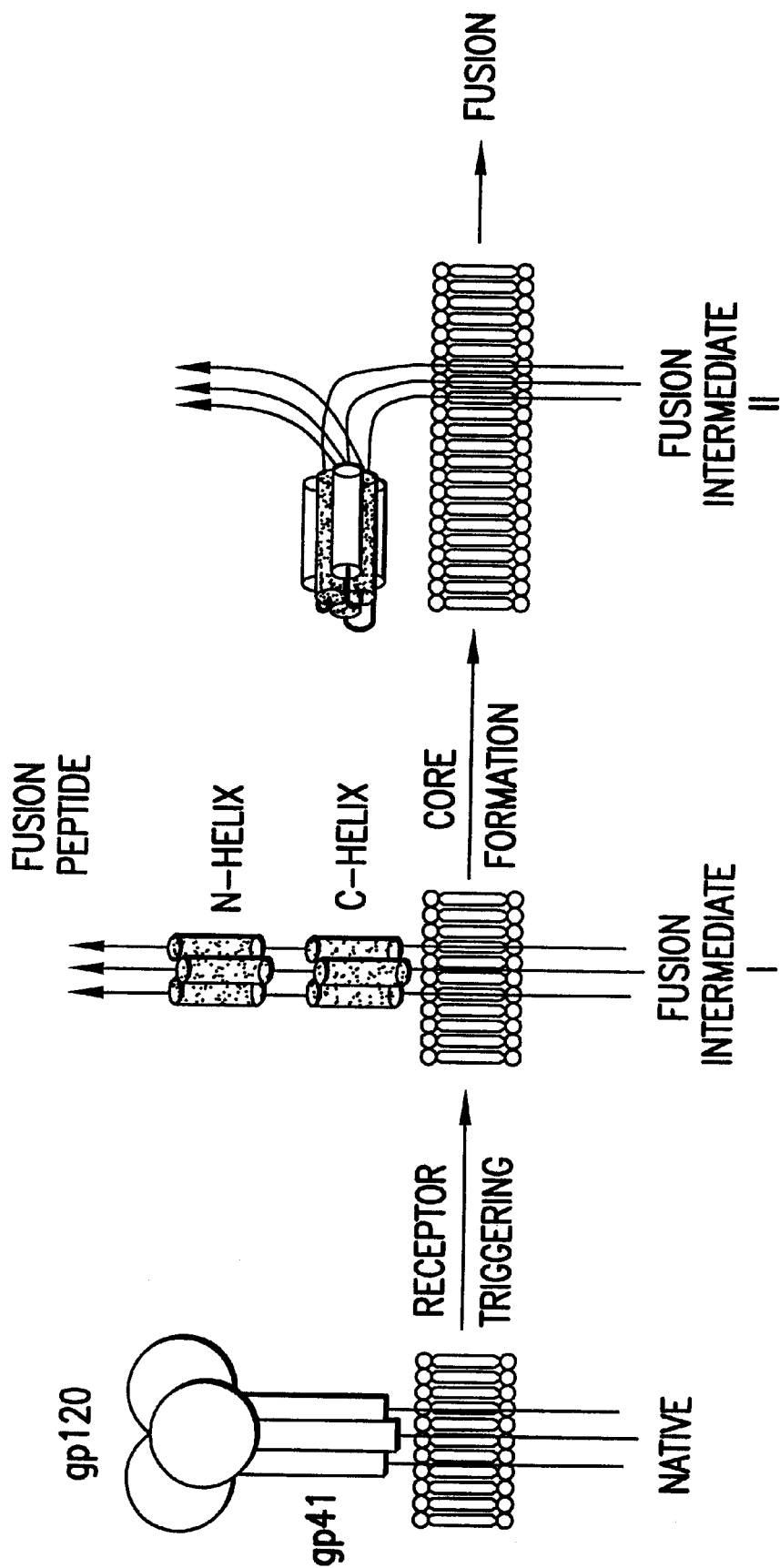
FIG. 5 is a schematic representation of gp41 intermediate structures formed during virus entry. Fusion intermediate I forms immediately following receptor binding and shows the ectodomain in an extended form. Fusion intermediate II shows gp41 following core structure formation. The inhibitory peptides are believed to inhibit by interacting with the complementary regions of gp41 in a dominant-negative fashion.

The present invention is directed to a method of screening for inhibitors of viral entry structure formation. The present invention provides methods of screening for compounds that disrupt the formation of entry-relevant structures and conformations necessary for virus entry into virus permissive cells. The screening methods involve selectively triggering the formation of one or more critical entry intermediates in cell-surface-expressed viral envelope and probing for its formation. This can be accomplished as described herein.

In a first aspect, the present invention is directed to a screening assay for inhibitory compounds which involves determining the effect a candidate compound has on the formation of a conformational intermediate of viral entry and/or fusion. In particular, the method involves contacting a viral envelope protein or glycoprotein with a triggering agent and a candidate compound and thereafter measuring the effect that the candidate compound has on the formation of said conformational intermediate.

The effect of a candidate compound on conformational intermediate formation can be measured by antibody binding to these conformational intermediates. This is carried out by incubating the mixture with specific antibodies to determine whether the amount of antibody binding to a conformational intermediate of viral entry and/or fusion is increased or decreased due to the presence of the candidate compound. Alternatively, the effect of a candidate compound on conformational intermediate formation can be measured by antibody binding to viral envelope protein or glycoprotein as it exists prior to contact with a triggering agent. The antibodies employed in the assay are an important element of the claimed invention. In one aspect, the detection antibodies that bind to epitopes present in one or more of the entry-relevant structures or conformations (conformational intermediates) should not substantially bind to regions on the viral envelope protein or glycoprotein in its non-triggered state (prior to contact with a triggering agent). Alternatively, the detection antibodies that bind to epitopes present in the viral envelope protein or glycoprotein should not substantially bind to epitopes present in one or more of the entry-relevant structures or conformations (conformational intermediates).

A preferred method of the invention comprises the following steps:
 a. mixing, in an aqueous, buffered solution:
   i. a viral envelope protein or glycoprotein in association with a lipid bilayer, wherein said envelope protein or glycoprotein is necessary and sufficient for viral entry in an intact virus, and wherein said envelope protein or glycoprotein is capable of interacting with one or more receptors on a virus permissive cell;
   ii. one or more virus permissive cells, one or more insoluble or soluble receptors from said virus permissive cells, or a combination thereof; and
   iii. a test compound;
 b. measuring the effect of the test compound upon the formation of one or more entry-relevant structures or conformations necessary for virus entry into virus permissive cells.

In one aspect of the invention, step b is performed by:
 adding one or more optionally detectably-labeled antibodies that preferentially bind an epitope that is present in a conformational or structural intermediate in a viral-entry event; and
 measuring the amount of antibody binding.

In another aspect of the invention, step b is performed by:
 adding one or more optionally detectably-labeled antibodies that preferentially bind an epitope that is present in a viral membrane protein or glycoprotein wherein said viral membrane protein or glycoprotein is not in contact with a triggering agent; and
 measuring the amount of antibody binding.

In either aspect, the method optionally further comprises:
 comparing the measured amount of antibody binding to a standard value.

Preferably, step a. comprises incubating reagent i. and reagent iii. for about 10 minutes to about 120 minutes, more preferably about 45 to about 90 minutes. Useful concentration ranges of test compound include from about 0.1 µg/mL to about 100 µg/mL. Useful concentration ranges of viral envelope protein or glycoprotein vary widely and may depend upon the manner upon which the viral envelope protein or glycoprotein is provided as discussed below.

Useful viral envelope proteins or glycoproteins are those proteins and/or glycoproteins that have one or more domains that participate in the entry event of a virus into a virus permissive cell. For instance, HIV-1 includes the envelope glycoproteins gp120/gp41. The envelope glycoprotein gp41 includes an N-helical domain and C-helical domain that participate in forming entry-relevant intermediate structures required for HIV fusion and entry into HIV-permissive cells (for example, lymphocytes). Other viruses, such as RSV, parainfluenza virus type 3 (HPIV-3), measles virus, and influenza virus include functionally similar envelope glycoprotein primary and secondary structure which form intermediate structures and conformations that mediate viral fusion and entry. The protein or glycoprotein is associated with an appropriate lipid bilayer system.

For purposes of the invention, a viral envelope protein or glycoprotein can be in association with a lipid bilayer in a number of different ways, so long as the viral envelope protein or glycoprotein exists in one or more conformations similar to a conformation that the protein or glycoprotein exists in its native environment. In the present invention, it is important that the protein or glycoprotein be in an environment which allows the protein or glycoprotein to form "entry-relevant" structures and conformations as defined herein.

Useful lipid bilayer systems include cells, virions, pseudovirions or other appropriate membrane vesicles or liposomes "expressing" either a viral envelope protein or glycoprotein. The envelope viral protein or glycoprotein will typically have one or more membrane-associating domains and one or more transmembrane domains. Examples of reagent i in the method of the invention include: cells transfected such that they surface express membrane associated envelope protein or glycoprotein, cells infected with replication defective viral particles and surface expressing membrane associated envelope protein or glycoprotein, inactivated virus particles, and pseudovirions.

The method of the present invention can be applied to viruses where a transmembrane protein or glycoprotein forms structures, conformations, and complexes that are involved with virus entry, including but not limited to, HIV-1, HIV-2, HTLV-I, HTLV-II, respiratory syncytial virus (RSV), parainfluenza virus type 3 (HPIV-3), Newcastle disease virus, feline immunodeficiency virus (FIV); human influenza viruses, and measles virus.

The method of the present invention requires a triggering agent. The triggering agent interacts with the lipid bilayer/membrane-associated envelope protein or glycoprotein system to induce entry-relevant structural or conformational changes in the transmembrane or fusion protein of the viral envelope system. Reagent ii in the methods described above serves as a triggering agent. The triggering agent for viral fusion and entry for a particular virus is typically a virus permissive cell, an insoluble or soluble receptor from said cell, or a functional fragment of said receptor. For purposes of the present invention, a "virus-permissive cell" is a cell into which a particular virus typically can enter and infect.

Useful virus permissive cells, or insoluble or soluble receptors from said virus permissive cells are dictated by the particular virus, and the host cells which are permissive to fusion and entry of the particular virus. For example, for HIV-1, permissive cells include lymphocytes. Soluble and insoluble CD4 receptors on the lymphocytes are also useful in the present invention as a triggering agent, as are certain chemokines receptors, such as, CCR5, CXCR4 or mixtures thereof or other chemokine receptors that have been shown to facilitate HIV-1 fusion to CD-4 bearing cells. For some HIV strains, binding to CD4 is sufficient to trigger the formation of entry-relevant structures and conformations while for other HIV strains, binding to a secondary receptor (usually the CCR5 or the CXCR4 chemokine receptor) is required.

Useful triggering agents for other viruses include the permissive cell lines for a particular virus. For RSV, HEp2 cells are useful permissive cells. For measles virus, Vero cells are useful permissive cells. For HIPV-3, HEp2 are useful permissive cells. Soluble and insoluble receptors from these cells may also be employed.

Useful concentrations of triggering agent vary depending upon whether the triggering agent is provided as a cell or as a soluble or insoluble receptor. Moreover, concentrations will vary depending upon the particular virus and its complementary receptor or trigger. In general, a useful concentration range for reagent ii. is from about 0.1 $\mu$g/mL of receptor protein to about 100 $\mu$g/mL of receptor protein, preferably from about 0.1 $\mu$g/mL to about 10 $\mu$g/mL. Note that the concentrations are expressed in terms of the receptor protein. Such concentrations can be determined by methods known to those of skill in the art. The triggering agent is preferably incubated with a mixture of test compound and viral envelope protein or glycoprotein for a period of about 10 minutes to about 120 minutes, preferably about 30 to about 90 minutes.

In the absence of an inhibitor, the incubation of viral envelope protein or glycoprotein and triggering agent will cause the viral envelope protein or glycoprotein to undergo conformational changes through one or more structural intermediates that are necessary for viral fusion and entry into the virus permissive cell.

In one aspect, the antibody that is added in step b. is capable of substantially binding to one or more intermediate structures (the structural or conformational epitopes). The antibody is also characterized by substantially lower binding to epitopes on the viral envelope protein or glycoprotein in the absence of a triggering agent. Useful antibodies include antibodies raised against combinations of peptides, and recombinant proteins and proteins and protein fragments that accurately model entry-relevant envelope determinants. Methods of generating these antibodies and determining their binding are discussed below.

In another aspect, useful antibodies are those antibodies that bind to an epitope that (a) is present on a viral envelope protein or glycoprotein prior to contact with a triggering agent, and (b) is lost following contact of the viral envelope protein or glycoprotein with a triggering agent. Methods of generating these antibodies and determining their binding are discussed below.

Several methods can be used to detect binding of the antibodies in the methods of the present invention, including immunoprecipitation analysis, flow cytometry, fluorescence microscopy, or fluorometry. In addition, enzyme linked immunosorbent assay (ELISA) and radioimmunoassay (RIA) can be employed.

The antibodies are optionally labeled with a detectable label. Suitable labels are known in the art and include enzyme labels, such as, alkaline phosphatase, horseradish peroxidase, and glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine. Alternatively, the antibodies can be derivatized with a moiety that is recognized by a separately-added label, for example, biotin. Techniques for chemically modifying antibodies with these labels are well-known in the art.

The method optionally further comprises comparing the amount of antibody binding to a standard value. Antibody binding can be measured and expressed in a number of ways that are known to one of ordinary skill in the art. Using an antibody that preferentially binds an entry-relevant intermediate conformation or structure, compounds that inhibit viral fusion and entry by disrupting relevant-entry conformations will decrease the amount of antibody that is bound to reagent i., and therefore increase the amount of antibody in a free state when compared to a system without an inhibitor. Using an antibody that preferentially binds a to viral envelope protein or glycoprotein in a non-triggered state, compounds that inhibit viral fusion and entry by disrupting relevant-entry conformations will cause the amount of antibody that is bound to reagent i to be similar to the amount of antibody that is bound to reagent i in a system without an inhibitor.

A specific embodiment of the invention is directed to a method for determining compounds which disrupt formation of one or more critical gp41 entry-relevant structures or conformations, and thereby block HIV entry. The gp41 six-helix bundle which forms in response to CD4/gp 120 binding constitutes one such critical entry structure. Antibodies specific for the six-helix bundle are used to determine the ability of small molecules to block its formation.

Cells, virions, or other appropriate membrane vesicles or liposomes expressing the HIV-1 envelope glycoproteins gp120/gp41 are incubated in the presence or absence of potential anti-viral compounds (test compounds) and receptors (triggering agent(s)), and then assayed for changes in conformation of gp41 using poly- and/or monoclonal sera raised against a mixture of peptides or recombinant proteins mimicking the six-helix bundle structure (for example, a mixture of P15 and P16). Test compounds that inhibit formation of an "entry-relevant structure," such as a six-helix bundle, would cause a decrease in binding of these antibodies.

Several methods can be used to detect binding of the antibodies in these assay, including ELISA, immunoprecipitation analysis, flow cytometry, fluorescence microscopy, or fluorometry.

Thus, in one aspect of the invention the method comprises:

incubating cells expressing at least one HIV envelope glycoprotein or fragment thereof with a test compound; thereafter incubating the resultant mixture with a soluble form of at least one cell surface receptor or fragment thereof in an amount sufficient to activate the at least one glycoprotein or fragment thereof for viral entry to create a second mixture; and determining the effect of said test compound on the formation of one or more structural or conformational intermediates in a viral-entry event.

The determining step can be performed by:

adding one or more optionally detectably-labeled antibodies that bind an epitope that is a structural or conformational intermediate in a viral-entry event; and measuring the amount of antibody binding.

Alternatively, the determining step can be performed by:

adding one or more optionally detectably-labeled antibodies that preferentially bind an epitope that is present in a viral membrane protein or glycoprotein wherein said viral membrane protein or glycoprotein is not in contact with a triggering agent; and measuring the amount of antibody binding.

The method optionally further comprises comparing the measured amount of antibody binding to a standard value.

In another embodiment, the at least one viral envelope protein or fragment thereof is a glycoprotein or fragment thereof. In another embodiment, the glycoprotein or fragment thereof is the HIV-1 gp41/gp120 complex or fragment thereof in association with a lipid membrane or bilayer.

The invention further relates to a method of screening for a viral fusion inhibitor, comprising:

incubating at least one non-infectious viral particle having at least one surface envelope glycoprotein or fragment thereof exterior to the viral membrane with a test compound;

thereafter incubating the resultant mixture with a soluble form of at least one cell surface receptor or fragment thereof in an amount sufficient to activate the glycoprotein or fragment thereof for viral entry to create a second mixture, determining the effect of said test compound on the formation of one or more structural or conformational intermediate in a viral-entry event.

The determining step can be performed by:

adding one or more optionally detectably-labeled antibodies that bind an epitope that is a structural or conformational intermediate in a viral-entry event;

and measuring the amount of antibody binding.

Alternatively, the determining step can be performed by:

adding one or more optionally detectably-labeled antibodies that preferentially bind an epitope that is present in a viral membrane protein or glycoprotein wherein said viral membrane protein or glycoprotein is not in contact with a triggering agent; and measuring the amount of antibody binding.

The method optionally further comprises comparing the measured amount of antibody binding to a standard value.

In one embodiment, the at least one surface envelope glycoprotein or fragment thereof is the HIV-1 gp41/gp120 complex or fragment thereof.

In another embodiment, the cells expressing the envelope glycoprotein or fragment thereof are cells infected with a recombinant vaccinia virus expressing the HIV-1 envelope protein or fragment thereof. In another embodiment, the cells expressing the envelope glycoprotein or fragment thereof are cells transformed with a vector expressing the HIV-1 envelope protein or fragment thereof. In another embodiment, the cells expressing the envelope glycoprotein or fragment thereof are infected with a replication defective viral particle or pseudovirion bearing at least one envelope protein or fragment thereof from at least one laboratory-adapted or primary viral isolate.

More specifically, useful reagents in the present invention include non-infectious HIV-1 particles (an example being 8E5/LAV virus (Folks, T. M., et al., *J. Exp. Med.* 164:280–290 (1986); Lightfoote, M. M., et al., *J. Virol.* 60:771–775 (1986); Gendelman, H. E., et al., *Virology* 160:323–329 (1987))) or pseudovirions bearing the envelope glycoprotein or fragment thereof from at least one laboratory-adapted or primary HIV-1 isolate (Haddrick, M., et al., *J. Virol. Methods* 61:89–93 (1996); Yamshchikov, G. V., et al., *Virology* 21:50–58 (1995)).

The 8E5/LAV cell line produces an intact virion expressing functional envelope in a non-replicating system. A soluble form or fragment thereof of the primary HIV-1 receptor, CD4, is added (sCD4). The addition of sCD4 activates the envelope glycoprotein or fragment thereof for viral entry by binding to and triggering gp120 which in turn triggers fusion-active forms of gp41.

In another alternative embodiment, cells expressing the at least one viral envelope protein, e.g., cells infected with a recombinant vaccinia virus expressing the HIV-1 envelope protein or fragment thereof (Earl, P. L., et al., *J. Virol.* 65:31–41 (1991); Rencher, S. D., et al., *Vaccine* 5:265–272 (1997); Katz, E. and Moss, B., *AIDS Res. Hum. Retroviruses* 13:1497–1500 (1997)), can be used. The envelope-expressing cells are incubated with a triggering agent.

As another alternative embodiment, in the methods described above, CD4 and chemokine expressing cell lines can be substituted for lymphocytes or soluble CD4 (sCD4). By this method, reagent i and test compound are incubated with a cell line expressing CD4 or an appropriate chemokine receptor such as CR4, CCR5 or CXCR4 which serves to trigger the formation of entry-relevant structures and conformations.

The methods described above can be applied to other viruses where the envelope proteins form similar complexes that are critical to virus entry including, but not limited to, HIV-2, HTLV-I, HTLV-II, respiratory syncytial virus (RSV), human influenza virus, measles virus, parainfluenza virus type 3 (HPIV-3), Newcastle disease virus, and feline immunodeficiency virus (FIV).

The invention includes the novel compounds detected in these assays that may include but are not limited to small molecules, peptides, antibodies and antibody fragments.

The invention is also directed to novel inhibitors identified by these methods, which can be small molecules, peptides, proteins, antibodies and antibody fragments, or derivatives thereof. These inhibitors are suitable for inhibiting or preventing infection by various viruses including HIV-1 and/or the other viruses listed above. These inhibitors can be used to treat humans infected with HIV-1 or the other viruses, or used to prevent infection by HIV-1 or the other viruses. The invention also includes the inhibitors in suitable pharmaceutical compositions. These antiviral compounds can also be used to inactivate viruses in body fluids e.g. blood or blood components used for therapeutic purposes.

This invention also includes the use of the assays described above as diagnostic assays to detect antibodies in virus-infected individuals or virus-infected body fluids or tissues that inhibit entry-relevant conformational changes in one or more viral envelope proteins or glycoproteins. The presence of such antibodies in infected individuals or samples is of prognostic value.

Antibodies

The peptides and polypeptides useful in the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or from a native source. For example, a recombinantly produced polypeptide can be substantially purified by the one-step method described in Smith and Johnson, Gene 67:31–40 (1988). Alternatively, peptides can be synthesized using well-known peptide synthesis techniques.

In one aspect of the invention antibodies are raised by administering to a mammal a peptide or polypeptide comprising an amino acid sequence that is capable of forming a stable coiled-coil solution structure corresponding to or mimicking the heptad repeat region of gp41 which is located in the N-helical domain as defined herein. Peptides, or multimers thereof, that comprise amino acid sequences which correspond to or mimic solution conformation of the N-helical heptad repeat region of gp41 can be employed. The N-helical heptad repeat region of gp41 includes 4 heptad repeats. Preferably, the peptides comprise about 28 to 55 amino acids of the heptad repeat region of the extracellular domain of HIV gp41 (N-helical domain, (SEQ. ID NO:1)), or multimers thereof. The peptides can be administered as a small peptide, or conjugated to a larger carrier protein such as keyhole limpet hemocyanin (KLH), ovalbumin, bovine serum albumin (BSA) or tetanus toxoid. Peptides forming a stable coiled-coil solution structure corresponding to or mimicking the heptad repeat region of gp41 can be employed to form either polyclonal or monoclonal antibodies. To determine whether a particular peptide or multimer will possess a stable trimeric coiled-coil solution structure corresponding to or mimicking the heptad repeat region of gp41, the peptide can be tested according to the methods described in Wild, C., et al., Proc. Natl. Acad. Sci. USA 89:10537–10541 (1992), fully incorporated by reference herein.

Shown below is the sequence for residues of the HIV-1$_{LAI}$ gp41 protein that form the N-helical domain of the protein:

(SEQ. ID NO:1)
ARQLLSGIVQQQNNLLRAIEAQQHLLQLTVWGIKQLQARILAVERYLK

DQQLLGI

Two examples of useful peptides include the peptide P-17, which has the formula, from amino terminus to carboxy terminus, of:

(SEQ ID NO:2)
NH$_2$-NNLLRAIEAQQHLLQLTVWGIKQLQARILAVERYLKDQ-COOH;

and the peptide P-15, which has the formula, from amino terminus to carboxy terminus, of:

(SEQ ID NO:3)
NH$_2$-SGIVQQQNNLLRAIEAQQHLLQLTVWGIKQLQARIL-COOH.

These peptides are optionally coupled to a larger carrier protein, or optionally include a terminal protecting group at the N- and/or C-termini. Useful peptides further include peptides corresponding to P-17 or P-15 that include one or more, preferably 1 to 10 conservative substitutions, as described below. A number of useful N-helical region peptides are described herein.

Antibodies can also be raised by administering to a mammal a peptide or polypeptide comprising an amino acid sequence that corresponds to, or mimics, the transmembrane-proximal amphipathic α-helical segment of gp41 (C-helical domain, (SEQ ID NO:4)), or a portion thereof. Useful peptides or polypeptides include an amino acid sequence that is capable of forming a core six helix bundle when mixed with a peptide corresponding to the heptad repeat region of gp41, such as the peptide P-17. Peptides can be tested for the ability to form a core six helix bundle employing the system and conditions described in Chan, D. C., et al, Cell 89:263–273 (1997); Lu, M., et al., Nature Struct. Biol. 2:1075–1082 (1995), fully incorporated by reference herein.

Shown below is the amino acid sequence for residues of the HIV-1$_{LAI}$ gp41 protein that form the C-helical domain of the protein:

(SEQ ID NO:4)
WNNMTWMEWDREINNYTSLIHSLIEESQNQQEKNEQELLELDKWASL

WNWFNITNW

Preferred peptides or multimers thereof, that can be employed in this aspect of the invention comprise about 6 or more amino acids, preferably about 24–56 amino acids, of the extracellular C-helical domain of HIV gp41. The peptides can be administered as a small peptide, or conjugated to a larger carrier protein such as keyhole limpet hemocyanin (KLH), ovalbumin, bovine serum albumin (BSA) or tetanus toxoid. This transmembrane-proximal amphipathic α-helical segment is exemplified by the peptides P-16 and P-18, described below. Peptides or polypeptides comprising amino acid sequences that correspond to, or mimic, the transmembrane-proximal amphipathic α-helical segment of gp4 1, or a portion thereof, can be employed to form either polyclonal or monoclonal antibodies.

Examples of useful peptides for this aspect of the invention include the peptide P-18 which corresponds to a portion of the transmembrane protein gp41 from the HIV-1$_{LAI}$ isolate, and has the 36 amino acid sequence (reading from amino to carboxy terminus):

(SEQ ID NO:5)
NH$_2$-YTSLIHSLIEESQNQQEKNEQELLELDKWASLWNWF-COOH;

and the peptide P-16, which has the following amino acid sequence (reading from amino to carboxy terminus):

(SEQ ID NO:6)
NH$_2$-WMEWDREINNYTSLIHSLIEESQNQQEKNEQELL-COOH

These peptides are optionally coupled to a larger carrier protein. Useful peptides further include peptides corresponding to P-18 or P-16 that include one or more, preferably 1 to 10 conservative substitutions, as described below. In addition to the full-length P-18, 36-mer and the full length P-16, the peptides of this aspect of the invention may include truncations of the P-18 and P-16, as long as the truncations are capable of forming a six helix bundle when mixed with P-17 or P-15.

Antibodies can also be raised by administering to a mammal one or more peptides or polypeptides which comprise amino acid sequences that are capable of forming solution stable structures that correspond to, or mimic, the gp41 core six helix bundle. This bundle forms in gp41 by the interaction of the distal regions of the transmembrane protein, the heptad repeat region and the amphipathic α-helical region segment roughly corresponding to the N-helical domain and C-helical domain. The bundle structures that form in native virus are the result of a trimeric interaction between three copies each of the heptad repeat region and the transmembrane-proximal amphipathic α-helical segment. In the compositions useful in the present invention, peptide regions interact with one another to form a core six helix bundle. Useful are mixtures of peptides and polypeptides, including multimeric and conjugate structures, wherein said structures form a stable core helix solution structure.

Mixtures of (a) one or more peptides that comprise an amino acid sequence that corresponds to, or mimics, a stable coiled coil heptad repeat region of gp41; and (b) one or more peptides that comprise a region that corresponds to, or mimics, the transmembrane-proximal amphipathic α-helical segment of gp41 are contemplated. These mixtures are optionally chemically or oxidatively cross-linked to provide additional immunogenic structures that may or may not be solution stable. In addition to physical mixtures, and conventional cross-linking, the peptides (a) and (b) can be conjugated together via suitable linking groups, preferably a peptide residue having at least 2, preferably 2 to 25, amino acid residues. Preferred linking groups are formed from combinations of glycine and serine, or combinations of glycine and cysteine when further oxidative cross-linking is envisioned.

Exemplary embodiments include raising antibodies to physical mixtures of P-17 and P-18, P-15 and P-16, P-17 and P-16 or P-15 and P-18.

Antibodies can also be raised by administering to a mammal a composition including one or more novel peptides and proteins, herein referred to as conjugates, that mimic fusion-active transmembrane protein structures. These conjugates are formed from peptides and proteins that comprise:

(a) one or more amino acid sequences of 28 or more amino acids that are capable of forming a stable coiled-coil solution structure corresponding to or mimicking the heptad repeat region of gp41; and (b) one or more amino acid sequences that correspond to, or mimic, an amino acid sequence of the transmembrane-proximal amphipathic α-helical segment of gp41;

wherein said one or more sequences (a) and (b) are alternately linked to one another via a peptide bond (amide linkage) or by an amino acid linking sequence consisting of about 2 to about 25 amino acids. These peptides and proteins are preferably recombinantly produced.

These conjugates preferably fold and assemble into a structure corresponding to, or mimicking, an entry-relevant structure. Examples of the novel constructs or conjugates that can be formed include (reading from N-terminus to C-terminus):

(1) three tandem repeating units consisting of P-17-linker-P-18 (P-17-linker-P-18-linker-P-17-linker-P-18-linker-P-17-linker-P-18), (2) P-17-linker-P-18-linker-P-17, (3) P-18-linker-P-17-linker-P-18, (4) P-18-linker-P-17, (5) three tandem repeating units consisting of P-15-linker-P-16 (P-15-linker-P-16-linker-P-15-linker-P-16-linker-P-15-linker-P-16), (6) P-15-linker-P-16-linker-P-15, (7) P-16-linker-P-15-Iinker-P-16, (8) P-16-linker-P-15; and (9) P-15-linker-P-16;

wherein each linker is an amino acid sequence, which may be the same or different, of from about 2 to about 25, preferably 2 to about 16 amino acid residues. Preferred amino acid residues include glycine and serine, for example $(GGGGS)_X$, (SEQ ID NO:7) wherein x is 1, 2, 3, 4, or 5, or glycine and cysteine, for example $(GGC)_y$, where y is 1, 2, 3, 4 or 5. In any of the described constructs, P-15 and P-17 are interchangeable and P-16 and P-18 are interchangeable. An example of such a construct is shown in FIG. 7.

The phrase "entry-relevant" as employed herein, refers to particular molecular conformations or structures that occur or are exposed following interaction of HIV with the cell surface during viral entry, and the role of particular amino acid sequences and molecular conformations or structures in viral entry.

The term "HIV" as used herein refers to all strains and isolates of human immunodeficiency virus type 1. The constructs of the invention were based upon HIV-1 gp41, and the numbering of amino acids in HIV proteins and fragments thereof given herein is with respect to the HIV-$1_{LAI}$ isolate. However, it is to be understood, that while HIV-1 viral infection and the effects of the present invention on such HIV-1 infection are being used herein as a model system, the entry mechanism that is being targeted is relevant to all strains and isolates of HIV-1. Hence the invention is directed to "comprehensive screening" methods.

The phrase "heptad repeat" or "heptad repeat region" as employed herein, refers to a common protein motif having a 4–3 repeat of amino acids, commonly leucine and/or isoleucine, and is often associated with alpha-helical secondary structure. The "heptad repeat" can be represented by the following sequence:

$$—(AA_1—AA_2—AA_3—AA_4—AA_5—AA_6—AA_7)—$$

where $AA_1$ and $AA_4$ are each one of leucine or isoleucine; while $AA_2$, $AA_3$, $AA_5$, $AA_6$, and $AA_7$ can be any amino acid. See, Wild, C., et al., *Proc. Natl. Acad. Sci. USA* 89:10537–10541(1992).

Peptides are defined herein as organic compounds comprising two or more amino acids covalently joined by peptide bonds. Peptides may be referred to with respect to the number of constituent amino acids, i.e., a dipeptide contains two amino acid residues, a tripeptide contains three, etc. Peptides containing ten or fewer amino acids may be referred to as oligopeptides, while those with more than ten amino acid residues are polypeptides.

The complete gp41 amino acid sequence (HIV-1 Group M: Subtype B Isolate: LAI, N to C termini) is:

```
AVGIGALFLGFLGAAGSTMGARSMTLTVQARQLLSGIVQQQNNLLRAIEA          (SEQ ID NO:8)

QQHLLQLTVWGIKQLQARILAVERYLKDQQLLGIWGCSGKLICTTAVPW

NASWSNKSLEQIWNNMTWMEWDREINNYTSLIHSLIEESQNQQEK

NEQELLELDKWASLWNWFNITNWLWYIKIFIMIVGGLVGLRIVFAVLSIV

NRVRQGYSPLSFQTHLP-TPRG-PDRPEGIEEEGGERDRDRSIRLVNGSL

ALIWDDLRSLCLFSYHRLRDLLLIVTRIVELLGRRGWEALKYWW

NLLQYWSQELKNSAVSLLNATAIAVAEGTDRVIEVVQGACRAIRHIPRRIR

QGLERILL.
```

The N-terminal helical region of gp41 is:

```
                                                          (SEQ ID NO:1)
ARQLLSGIVQQQNNLLRAIEAQQHLLQLTVWGIKQLQARILAVERYLKDQ

QLLGI
```

Shown below is the sequence for residues 558–595 (SEQ ID NO:7) of the HIV-1$_{LAI}$ gp41 protein in the N-helical domain of the protein. The a and d subscripts denote the 4–3 positions of the heptad repeat.

as measured by circular dichroism (Wild, C. et al., *PNAS* 89:10537–10541 (1992) are considered compatible with their use in the invention.

When modeled as a peptide, the C-helical region of gp41 is not structured. However, when mixed with the N-peptide, the C-peptide does take on a α-helical secondary structure as part of the six-helical core complex. The structure forms in vitro on mixing N- and C-helical peptides and can be characterized spectrophotometrically (Lu, M., et al., *Nat. Struct. Biol.* 2:1075–1082 (1995)). The initial determination of the effect of primary sequence deletions, insertions and

```
N N L L R A I E A Q Q H L L Q L T V W G I K Q L Q A R I L A V E R Y L K D Q    (SEQ ID NO:2)
    d       a       d       a       d       a       d       a       d       a 571             578             585
```

The C-terminal helical region of gp41 is:

```
                                                                              (SEQ ID NO:4)

WNNMTWMEWDREINNYTSLIHSLIEESQNQQEKNEQELLELDKWASL

WNWFNITNW
```

Shown below is the amino acid sequence for residues 643–678 of the HIV-1$_{LAI}$ gp41 protein in the C-helical domain of the protein.

```
Y T S L I H S L I E E S Q N Q Q E K N E Q E L L E L D K-     (SEQ ID NO:4)
W A S L W N W F d       a       d       a       d       a       d       a       d       a 647             654             661
```

Peptides modeling the N and C-helical domains of HIV-1 gp41 can be constructed from multiple strains of HIV, and can include amino acid deletions, insertions and substitutions that do not destroy the ability of the resulting peptides to elicit antibodies against entry-relevant gp41 structures and conformations when employed alone or in combination with other peptides of the invention.

The effect of such changes on the ability of peptides modeling the N-helical region of gp41 to elicit the desired antibody response can be determined spectrophotometrically. Deletions, insertions and substitutions within the primary sequence of N-helical peptides which do not alter the ability of the peptide to form α-helical secondary structure substitutions on C-helix structure may be performed by analyzing the ability of the variant C-peptides to interact with a structured form of the N-peptide to form the six-helix bundle. C-peptides which interact to forms this structure are considered compatible with their use in the invention. This analysis may be carried out using circular dichroism.

Examples of N-helical Domain Peptide Sequences (All sequences are listed from N-terminus to C-terminus.) from different HIV strains include, but are not limited to the following peptides:

HIV-1 Group M: Subtype B Isolate: LAI
ARQLLSGIVQQQNNLLRAIEAQQHLLQLTVWGIKQLQARILAVERYLK    (SEQ ID NO:1)
DQQLLGI
(SEQ ID NO:1)
SGIVQQQNNLLRAIEAQQHLLQLTVWGIKQLQARILAVERYLKDQ       (SEQ ID NO:9)

P15   SGIVQQQNNLLRAIEAQQHLLQLTVWGIKQLQARIL          (SEQ ID NO:3)

P-17  NNLLRAIEAQQHLLQLTVWGIKQLQARILAVERYLKDQ        (SEQ ID NO:2)

Subtype B Isolate: ADA
SGIVQQQNNLLRAIEAQQHLLQLTVWGIKQLQARVLALERYLRDQ       (SEQ ID NO:10)

SGIVQQQNNLLRAIEAQQHLLQLTVWGIKQLQARVL                (SEQ ID NO:11)

NNLLRAIEAQQHLLQLTVWGIKQLQARVLALERYLRDQ              (SEQ ID NO:12)

Subtype B Isolate: JRFL
SGIVQQQNNLLRAIEAQQRMLQLTVWGIKQLQARVLAVERYLGDQ       (SEQ ID NO:13)

SGIVQQQNNLLRAIEAQQRMLQLTVWGIKQLQARVL                (SEQ ID NO:14)

NNLLRAIEAQQRMLQLTVWGIKQLQARVLAVERYLGDQ              (SEQ ID NO:15)

Subtype B Isolate: 89.6
SGIVQQQNNLLRAIEAQQHMLQLTVWGIKQLQARVLALERYLRDQ       (SEQ ID NO:16)

SGIVQQQNNLLRAIEAQQHMLQLTVWGIKQLQARVL                (SEQ ID NO:17)

NNLLRAIEAQQHMLQLTVWGIKQLQARVLALERYLRDQ              (SEQ ID NO:18)

Subtype C Isolate: BU910812
SGIVQQQSNLLRAIEAQQHMLQLTVWGIKQLQARVLAIERYLRDQ       (SEQ ID NO:19)

SGIVQQQSNLLRAIEAQQHMLQLTVWGIKQLQARVL                (SEQ ID NO:20)

SNLLRAIEAQQHMLQLTVWGIKQLQARVLAIERYLRDQ              (SEQ ID NO:21)

Subtype D Isolate: 92UG024D
SGIVQQQNNLLRAIEAQQHLLQLTVWGIKQLQARVLAVESYLKDQ       (SEQ ID NO:22)

SGIVQQQNNLLRAIEAQQHLLQLTVWGIKQLQARVL                (SEQ ID NO:11)

NNLLRAIEAQQHLLQLTVWGIKQLQARVLAVESYLKDQ              (SEQ ID NO:23)

Subtype F Isolate: BZ163A
SGIVQQQSNLLRAIEAQQHLLQLTVWGIKQLQARVLAVERYLQDQ       (SEQ ID NO:24)

SGIVQQQSNLLRAIEAQQHLLQLTVWGIKQLQARVL                (SEQ ID NO:25)

SNLLRALEAQQHLLQLTVWGIKQLQARVLAVERYLQDQ              (SEQ ID NO:26)

Subtype G Isolate: FI.HH8793
SGIVQQQSNLLRAIEAQQHLLQLTVWGIKQLQARVLALERYLRDQ       (SEQ ID NO:27)

SGIVQQQSNLLRAIEAQQHLLQLTVWGIKQLQARVL                (SEQ ID NO:25)

SNLLRAIEAQQHLLQLTVWGIKQLQARVLALERYLRDQ              (SEQ ID NO:28)

Subtype H Isolate: BE.V1997
SGIVQQQSNLLRAIQAQQHMLQLTVWGVKQLQARVLAVERYLKDQ       (SEQ ID NO:29)

SGIVQQQSNLLRAIQAQQHMLQLTVWGVKQLQARVL                (SEQ ID NO:30)

SNLLRAIQAQQHMLQLTVWGVKQLQARVLAVERYLKDQ              (SEQ ID NO:31)

Subtype J Isolate: SE.SE92809
SGIVQQQSNLLKAIEAQQHLLKLTVWGIKQLQARVLAVERYLKDQ       (SEQ ID NO:32)

SGIVQQQSNLLKAIEAQQHLLKLTVWGIKQLQARVL                (SEQ ID NO:33)

SNLLKAIEAQQHLLKLTVWGIKQLQARVLAVERYLKDQ              (SEQ ID NO:34)

Group N Isolate: CM.YBF30
SGIVQQQNILLRAIEAQQHLLQLSIWGIKQLQAKVLAIERYLRDQ       (SEQ ID NO:35)

SGIVQQQNILLRAIEAQQHLLQLSIWGIKQLQAKVL                (SEQ ID NO:36)

NILLRAIEAQQHLLQLSIWGIKQLQAKVLAIERYLRDQ              (SEQ ID NO:37)

-continued

Group O Isolate: CM.ANT70C
KGIVQQQDNLLRAIQAQQQLLRLSxWGIRQLRARLLALETLLQNQ (SEQ ID NO:38)

KGIVQQQDNLLRAIQAQQQLLRLSxWGIRQLRARL (SEQ ID NO:39)

DNLLRAIQAQQQLLRLSxWGIRQLRARLLALETLLQNQ (SEQ ID NO:40)

Examples of C-helical Domain Peptide Sequences (All sequences are listed from N-terminus to C-terminus.) from different HIV strains include, but are not limited to the following peptides:

HIV-1 Group M: Subtype B Isolate: LAI
(SEQ ID NO:4)
WNNMTWMEWDREINNYTSLIHSLIEESQNQQEKNEQELLELDKWASL

WNWFNITNW (SEQ ID NO:41)
WMEWDREINNYTSLIHSLIEESQNQQEKNEQELLELDKWASLWNWF (SEQ ID NO:16)
P16 WMEWDREINNYTSLIHSLIEESQNQQEKNEQELL (SEQ ID NO:5)
P-18 YTSLIHSLIEESQNQQEKNEQELLELDKWASLWNWF

Subtype B Isolate: ADA
(SEQ ID NO:42)
WMEWEREIENYTGLIYTLIEESQNQQEKNEQDLLALDKWASLWNWF (SEQ ID NO:43)
WMEWEREIENYTGLIYTLIEESQNQQEKNEQDLL (SEQ ID NO:44)
YTGLIYTLIEESQNQQEKNEQDLLALDKWASLWNWF Subtype B Isolate: JRFL
(SEQ ID NO:45)
WMEWEREIDNYTSEIYTLIEESQNQQEKNEQELLELDKWASLWNWF (SEQ ID NO:46)
WMEWEREIDNYTSEIYTLIEESQNQQEKNEQELL (SEQ ID NO:47)
YTSEIYTLIEESQNQQEKNEQELLELDKWASLWNWF Subtype B Isolate: 89.6
(SEQ ID NO:48)
WMEWEREIDNYTDYIYDLLEKSQTQQEKNEKELLELDKWASLWNWF (SEQ ID NO:49)
WMEWEREIDNYTDYIYDLLEKSQTQQEKNEKELL (SEQ ID NO:50)
YTDYIYDLLEKSQTQQEKNEKELLELDKWASLWNWF Subtype C Isolate: BU910812
(SEQ ID NO:51)
WIQWDREISNYTGIIYRLLEESQNQQENNEKDLLALDKWQNLWSWF (SEQ ID NO:52)
WIQWDREISNYTGIIYRLLEESQNQQENNEKDLL (SEQ ID NO:53)
YTGIIYRLLEESQNQQENNEKDLLALDKWQNLWSWF Subtype D Isolate: 92UG024D
(SEQ ID NO:54)
WMEWEREISNYTGLIYDLIEESQIQQEKNEKDLLELDKWASLWNWF (SEQ ID NO:55)
WMEWEREISNYTGLIYDLIEESQIQQEKNEKDLL -continued (SEQ ID NO:56)
YTGLIYDLIEESQIQQEKNEKDLLELDKWASLWNWF Subtype F Isolate: BZ163A
(SEQ ID NO:57)
WMEWQKEISNYSNEVYRLIEKSQNQQEKNEQGLLALDKWASLWNWF (SEQ ID NO:58)
WMEWQKEISNYSNEVYRLIEKSQNQQEKNEQGLL (SEQ ID NO:59)
YSNEVYRLIEKSQNQQEKNEQGLLALDKWASLWNWF Subtype G Isolate: FI.HH8793
(SEQ ID NO:60)
WIQWDREISNYTQQIYSLIEESQNQQEKNEQDLLALDNWASLWTWF (SEQ ID NO:61)
WIQWDREISNYTQQIYSLIEESQNQQEKNEQDLL (SEQ ID NO:62)
YTQQIYSLIEESQNQQEKNEQDLLALDNWASLWTWF Subtype H Isolate: BE.V1997
(SEQ ID NO:63)
WMEWDRQIDNYTEVIYRLLELSQTQQEQNEQDLLALDKWDSLWNWF (SEQ ID NO:64)
WMEWDRQIDNYTEVIYRLLELSQTQQEQNEQDLL (SEQ ID NO:65)
YTEVIYRLLELSQTQQEQNEQDLLALDKWDSLWNWF Subtype J Isolate: SE.SE92809
(SEQ ID NO:66)
WIQWEREINNYTGIIYSLIEEAQNQQENNEKDLLALDKWTNLWNWFN (SEQ ID NO:67)
WIQWEREINNYTGIIYSLIEEAQNQQENNEKDLL (SEQ ID NO:68)
YTGIIYSLIEEAQNQQENNEKDLLALDKWTNLWNWFN Group N Isolate: CM.YBF30
(SEQ ID NO:69)
WQQWDEKVRNYSGVIFGLIEQAQEQQNTNEKSLLELDQWDSLWSWF (SEQ ID NO:70)
WQQWDEKVRNYSGVIFGLIEQAQEQQNTNEKSLL (SEQ ID NO:71)
YSGVIFGLIEQAQEQQNTNEKSLLELDQWDSLWSWF Group O Isolate: CM.ANT7OC
(SEQ ID NO:72)
WQEWDRQISNISSTIYEEIQKAQVQQEQNEKKLLELDEWASIWNWL (SEQ ID NO:73)
WQEWDRQISNISSTIYEEIQKAQVQQEQNEKKLL (SEQ ID NO:74)
ISSTIYEEIQKAQVQQEQNEKKLLELDEWASIWNWL The peptides and conjugates may be acylated at NH$_2$ terminus, and may be amidated at the COOH terminus.

Useful peptides from fusion-active regions from other viruses include the following peptides:

For RSV:
(SEQ ID NO:75)
GEPIINFYDPLVFPSDEFDASISQVHEKINQSLAFIRKSDELLHNVNAGK
STT

For HPIV3:
(SEQ ID NO:76)
YTPNDITLNNSVALDPIDISIELNKAKSDLEESKEWIRRSNQKLDSIGNW
HQSSTT

For measles virus:
(SEQ ID NO:77)
PDAVYLHRIDLGPPISLERLDVGTNLNAIAKLEDAKELLESSDQILRSMK Additional useful peptides are described in PCT Published Application No. Published PCT Application No. WO96/19495, and U.S. Pat. Nos. 6,020,459, 6,017,536, 6,013,263, 6,008,044 and 6,015,881, all of which are fully incorporated by reference herein. The peptides and conjugates may be acylated at the NH$_2$ terminus, and may be amidated at the COOH terminus. Mixtures and conjugates of the appropriate N-helical and C-helical peptides can be employed to generate antibodies to entry-relevant intermediate conformations and structures. The peptides can be employed alone to generate antibodies to the appropriate viral membrane protein or glycoprotein.

The peptides and conjugates may include conservative amino acid substitutions. Conserved amino acid substitutions consist of replacing one or more amino acids of the peptide sequence with amino acids of similar charge, size, and/or hydrophobicity characteristics, such as, for example, a glutamic acid (E) to aspartic acid (D) amino acid substitution. When only conserved substitutions are made, the resulting peptide is functionally equivalent to the peptide from which it is derived.

Peptide sequences defined herein are represented by one-letter symbols for amino acid residues as follows:

| A | alanine | L | leucine |
|---|---|---|---|
| R | arginine | K | lysine |
| N | asparagine | M | methionine |
| D | aspartic acid | F | phenylalamine |
| C | cysteine | P | proline |
| Q | glutamine | S | serine |
| E | glutamic acid | T | threonine |
| G | glycine | W | tryptophan |
| H | histidine | Y | tyrosine |
| I | isoleucine | V | valine |

The peptides and conjugates useful in the invention may include amino acid insertions which consist of single amino acid residues or stretches of residues ranging from 2 to 15 amino acids in length. One or more insertions may be introduced into the peptide, peptide fragment, analog and/or homolog.

The peptides and conjugates useful in the invention may include amino acid deletions of the full length peptide, analog, and/or homolog. Such deletions consist of the removal of one or more amino acids from the full-length peptide sequence, with the lower limit length of the resulting peptide sequence being 4 to 6 amino acids. Such deletions may involve a single contiguous portion or greater than one discrete portion of the peptide sequences.

Listed below are other useful antibodies:

the 2F5 monoclonal antibody which is the only broadly neutralizing antibody targeting gp41. This antibody maps to the linear amino acid sequence Glu-Leu-Asp-Lys-Trp-Ala (ELDKWA) in the ectodomain of obtainable from AIDS gp41 an epitope which is conserved in 72% of HIV-1 isolates; and monoclonal antibody, NC-1, which has been shown to bind the six-helix bundle in fusion-active gp41. NC-1, was generated and cloned from a mouse immunized with a mixture of peptides modeling the N- and C-helical domains of gp41. NC-1 binds specifically to both the α-helical core domain and the oligomeric forms of gp41. This conformation-dependent reactivity is dramatically reduced by point mutations within the N-terminal coiled-coil region of gp41 which impede formation of the gp41 core. NC-1 binds to the surfaces of HIV-1-infected cells only in the presence of soluble CD4.

Immunogen Preparation

Immunogens can be prepared by several different routes. The constructs can be generated from synthetic peptides. This involves preparing each sequence as a peptide monomer followed by post-synthetic modifications to generate the appropriate oligomeric structures. The peptides are synthesized by standard solid-phase methodology. To generate a trimeric coiled-coil structure, the P-17 peptide monomer is solubilized under conditions which favor oligomerization. These conditions include a 20 mM phosphate buffer, pH 4.5 and a peptide concentration of 100 µM (Wild, C., et al., *Proc. Natl. Acad. Sci. USA* 89:10537–10541 (1992)). The structure which forms under these conditions can be optionally stabilized by chemical crosslinking, for example using glutaraldehyde.

Alternatively, a protocol which makes use of intermolecular disulfide bond formation to stabilize the trimeric coiled-coil structure can be employed in order to avoid any disruptive effect the cross-linking process might have on the structural components of this construct. This approach uses the oxidation of appropriately positioned cysteine residues within the peptide sequence to stabilize the oligomeric structure. This requires the addition of a short linker sequence to the N terminus of the P-17 peptide. The trimeric coiled-coil structure which is formed by this approach will be stabilized by the interaction of the cysteine residues. The trimer is separated from higher order oligomeric forms, as well as residual monomer, by size exclusion chromatography and characterized by analytical ultracentrifugation. These covalently stabilized coiled-coil oligomers serve as the core structure for preparation of a six helix bundle.

To accomplish preparation of a six helix bundle, an excess of P-18 peptide or P-16 peptide is added to the N-helical coiled-coil trimer. After incubation the reaction mixture is subjected to a cross-linking procedure to stabilize the higher order products of the specific association of these two peptides. The desired material is isolated by size exclusion chromatography and can be characterized by analytical ultracentrifugation. The immunogen corresponding only to the P-18 or P-16 peptide requires no specific post-synthetic modifications. Using this approach, three separate target constructs are generated rapidly and in large amounts.

Another method for preparing target immunogens involves the use of a bacterial expression vector to generate recombinant gp41 fragments. The use of an expression vector to produce the peptides and polypeptides capable of forming the entry-relevant immunogens of the present invention adds a level of versatility to immunogen preparation.

New and modified forms of the antigenic targets are contemplated as the structural determinants of HIV-1 entry are better understood. The recombinant approach readily accommodates these changes. Also, this method of preparation allows for the ready modification of the various constructs (i.e. the addition of T- or B-cell epitopes to the recombinant gp41 fragments to increase immunogenicity). Finally, these recombinant constructs can be employed as a tool to provide valuable insights into additional structural components which form and function in gp41 during the process of virus entry.

A bacterial expression vector (kindly provided by Dr. Terrance Oas, Duke University) was developed specifically for the expression of small proteins. This plasmid, pTCLE-G2C, is based on pAED-4, a T7 expression vector. A modified TrpLE (Yansura, D. G., *Methods Enzymol.* 185:161–166 (1990)) fusion peptide (provided by Dr. Peter Kim) was inserted after the T7 promoter (Studier, F. W., et al., *Methods Enzymol.* 185:60–89 (1990)). There is an in frame Nde I site at the end of the TrpLE peptide that encodes for a methionine which gives rise to a cyanogen bromide (CNBr) cleavage site. This vector was used in an earlier study to express a recombinant form of the P-17 peptide (Calderone, T. L., et al., *J. Mol. Biol.* 262:407–412 (1996)) and has been modified to express the P-18 peptide and a P17/P18 chimeric protein.

To generate a six helix hydrophobic core structure, several combinations of the heptad repeat (for example, P-17 or P-15) region and the membrane proximal amphipathic α-helical (for example, P-16 or P-18) segment of gp41 are separated by a flexible linker of amino acid residues. For example, (GGGGS), (SEQ ID NO:7) where x is 1, 2 or 3 can be encoded into the vector. This is accomplished by standard PCR methods. The $(GGGGS)_x$ (SEQ ID NO:7) linker motif is encoded by a synthetic oligonucleotide which is ligated between the P-17 and P-18 encoding regions of the expression vector.

All constructions are characterized by multiple restriction enzyme digests and sequencing. The success of this approach to attain multicomponent interactions has been recently demonstrated (Huang, B., et al., *J. Immunol.* 158:216–225 (1997)).

Following expression, the recombinant gp41 fragments are isolated as inclusion bodies, cleaved from the leader sequence by cyanogen bromide, and separated from the leader by-product by size exclusion chromatography step (SUPERDEX 75). This protocol has been successfully used in the purification of large quantities of a modified form of the P-17 peptide (Calderone, T. L., et al., *J. Mol. Biol.* 262:407–412 (1996)). Recombinant constructs (2) and (3) are mixed in equalmolar quantities under non-denaturing conditions to generate a six-helix hydrophobic core structure. Constructs (1) and (4) will fold either intra- or intermolecularly to generate the same or similar structures. The desired product is purified by size exclusion chromatography on a SUPERDEX 75 FPLC column and characterized by molecular weight using a Beckman Model XL-A analytical ultracentrifuge.

Antibody Generation and Characterization

Generation and characterization of the antibodies against novel gp41 epitopes constitutes the second aspect of the invention. The experimental sera and monoclonal antibodies generated against the target immunogens are subjected to thorough biophysical and biological evaluation.

For the production of antibodies to a fusion-related, various host animals may be immunized by injection with a differentially expressed or pathway gene protein, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and Corynebacterium parvum.

Polyclonal antibodies are heterogeneous populations of antibody molecules derived from the sera of animals immunized with an antigen, such as a fusion-related peptide or mixtures or conjugates thereof as described above. For the production of polyclonal antibodies, host animals such as those described herein, may be immunized by injection with one or more peptides or recombinant proteins optionally supplemented with adjuvants.

Monoclonal antibodies, which are homogeneous populations of antibodies to a particular antigen, may be obtained by any technique which provides for the production of antibody molecules by continuous cell lines in culture. These include, but are not limited to the hybridoma technique of Kohler and Milstein, (*Nature* 256:495–497 (1975); and U.S. Pat. No. 4,376,110), the human B-cell hybridoma technique (Kosbor et al., *Immunology Today* 4:72 (1983); Cole et al., *Proc. Natl. Acad. Sci. USA* 80:2026–2030 (1983)), and the EBV-hybridoma technique (Cole et al., *Monoclonal Antibodies And Cancer Therapy,* Alan R. Liss, Inc., pp. 77–96 (1985)). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

Antibodies can be generated following established protocols. All small animal work (immunizations, bleeds, and hybridoma production) is carried out by standard methods known to those of skill in the art. A first set of immunogens consists of the peptide constructs P-15 or P-17 (capable of forming trimeric coiled-coil multimers, optionally stabilized by chemical cross-linking or oxidation), P-16 or P-18, and the P-17/P-18 mixture or P-15/P-16 mixture (wherein the peptides are optionally chemically or oxidatively cross-linked). In one set of experiments, the immunogens are conjugated to a carrier such as KLH.

Balb-c mice are immunized with each of these constructs. Mice can receive 100 μg of antigen conjugated to KLH. Following the initial immunization the animals receive a 100 μg boost on day 14 followed by 50 μg boosts on days 30 and 45. Bleeds occur two weeks following the final boost. Mice are also immunized with the recombinant constructs following the same outline as that for the peptide immunogens.

Alternative immunization approaches include the use of a recombinant adenovirus vector expressing all or part of the HIV-1 envelope glycoprotein gp120/gp41 as the primary immunogen followed by booster immunizations with the gp41 peptides, proteins or other constructs.

Samples can be screened by ELISA to characterize antibody binding. The antigen panel includes all experimental immunogens. Animals with sera samples which test positive for binding to one or more experimental immunogens are candidates for use in MAb production. Following this initial screen, one animal representing each experimental immunogen is selected for monoclonal antibody production.

Hybridoma supernatants are screened by ELISA, against structured and non-structured peptides and recombinants.

Samples that are ELISA negative or weakly positive are further characterized for IgG. If IgG is present the material is screened in the biophysical and biological assays. Strongly positive samples are screened for their ability to neutralize virus and bind envelope.

Antibodies are characterized in detail for their ability to bind HIV envelope under various conditions. For detection of antibody binding to native envelope, immunoprecipitations on Env-expressing cells and virions, both intact and lysed are performed using non-ionic detergents (Furata, RA et al., *Nat. Struct. Biol.* 5(4):276–279 (1997); White, J. M. and I. A. Wilson, *J. Cell Biol.* 105:2887–2894 (1987); Kemble, G. W., et al., *J. Virol.* 66:4940–4950 (1992)). Antibody binding to cell lysates and intact virions are also assayed in an ELISA format. Flow cytometry experiments are performed to determine binding to envelope expressing cells. Cross-competition experiments using other mapped Mabs, human sera, and peptides can also be performed. To characterize "triggers" to the conformational change, antibody binding to virus in the presence and absence of both sCD4 and target cells can be compared (White, J. M. and I. A. Wilson, *J. Cell Biol.* 105:2887–2894 (1987); Kemble, G. W., et al., *J. Virol.* 66:4940–4950 (1992)). Because the gp41 regions are highly conserved, epitope exposure using several different envelopes can be compared to discern possible differences in structure between primary, lab-adapted and genetically diverse virus isolates.

Figure 6A:
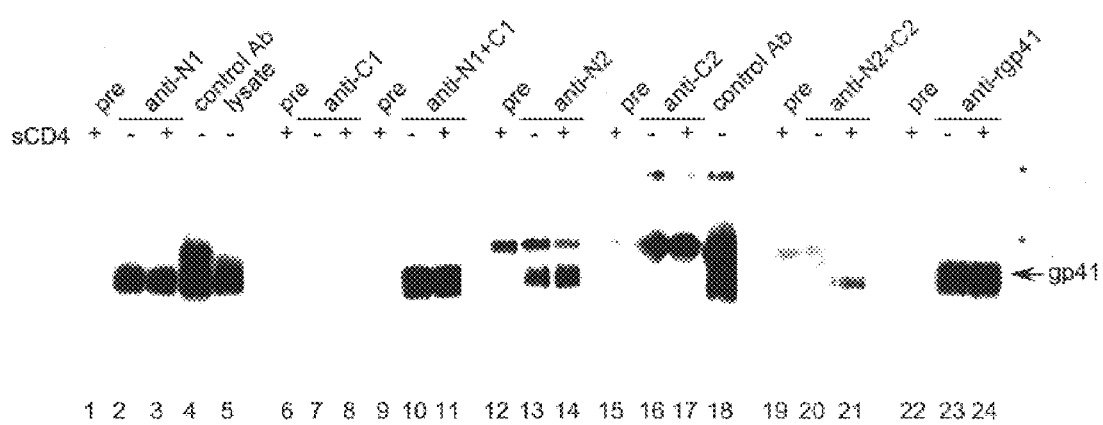
FIGS. 6A and 6B depict results from the lysate immunoprecipitation experiment and surface immunoprecipitation experiment, respectively.

Binding of peptide anti-sera to viral envelope is analyzed using immunoblot and immunoprecipitation (IP) assays. The results from these assays indicate that certain of the peptides and recombinant gp41 fragments accurately model fusion-active envelope determinants. The outcome of the Western blot studies roughly parallels the results from the ELISA assays with antisera raised against the more stable structured immunogens exhibiting the strongest binding to viral envelope determinants. In the lysate immunoprecipitation assay, polyclonal sera generated against the P15, P17, and P15/P17 mixed peptides as well as rgp41 precipitate the viral transmembrane protein. These results indicate that both the N-helical peptides and the mixture of the N- and C-helical peptides and rgp41 generate antibodies against structures found in native viral envelope (FIG. 6*a*).

Figure 6B:
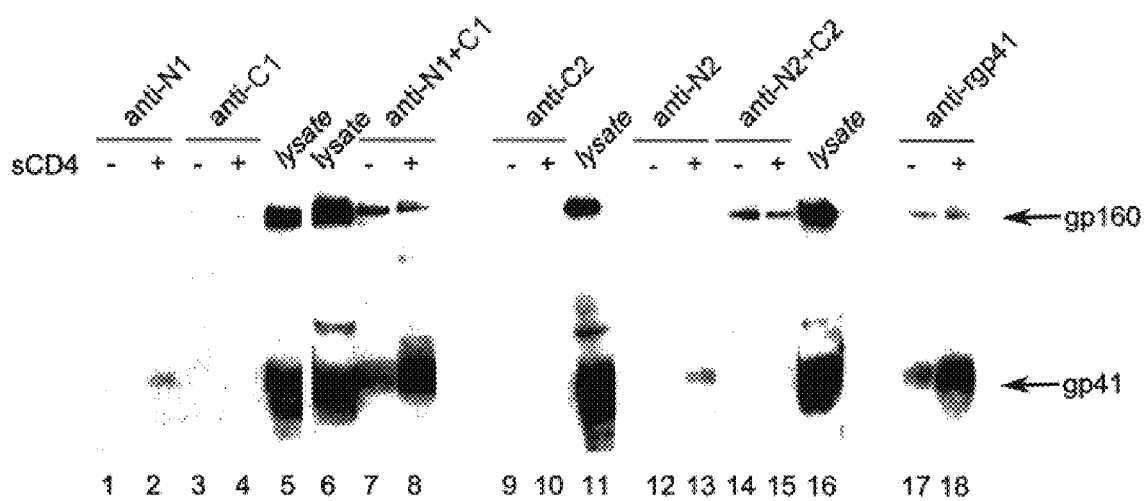

To further determine the ability of these immunogens to generate antibodies against fusion-active gp41 determinants a series of surface immunoprecipitation assays were carried out. These experiments allow characterization of antibody binding to cell-surface expressed envelope prior to and post receptor triggering. This assay format allows the study of epitopes found in both non-fusogenic and fusion-active envelope. In these experiments CD4 in both soluble and cell-expressed forms is utilized as a trigger for gp41 activation. The results indicate that both an N-helical peptides, the mixture of N- and C-helical peptides, and rgp41 generate antibodies against fusion-active structures (FIG. 6*b*). The greatly enhanced binding by antisera raised against the six-helix bundle post CD4 triggering is consistent with the proposed role of this gp41 determinant in virus entry.

ELISA Assay

Nunc Immulon 2 HB plates are coated with 1 µg/well of peptide. Approximately, 100 µl of sample at desired dilution are added in duplicate and allowed to incubate for 2 hrs at 37° C. Hybridoma supernatants are tested neat while polyclonal sera are assayed at an initial concentration of 1:100 followed by 4-fold dilutions. Following incubation, samples are removed and plates are washed with PBS+0.05% Tween-20, and 100 µl/well of diluted phosphatase-labeled secondary antibody (Sigma) is added. The secondary antibody-conjugate is diluted in blocking buffer to a final concentration of 1:1500 and added. Following incubation at room temperature, plates are washed and substrate (Sigma fast p-nitrophenyl phosphate) is added. Following development, plates are read at 405 nm.

Western blot Analysis

Commercial HIV-1 western blot strips are pre-wet with wash buffer (PBS+0.05% Tween-20). Samples are diluted in buffer (PBS, 0.05% Tween-20, 5% evaporated milk) to a final concentration of 1:5 for hybridoma supernatants and 1:200 for polyclonal sera and added to the strips. Following incubation (2 hrs with rocking), the strips are washed (3×5 min intervals) with wash buffer. Peroxidase-labeled secondary antibody (Kirkgaard & Perry Laboratories) is added at a concentration of 1:5000 and incubated with rocking for 1 h. Strips are washed again as described previously and TMB substrate is added. Color development is stopped by the addition of water.

Lysate Immunoprecipitation Assay

Hybridoma supernatants or immunosera are incubated overnight at 4° C. in 200 µl PBS containing 4.2 µl of HIV-1 IIIB cell lysate. The lysate is prepared from acute infection of the H9 cell line. Immune complexes are precipitated by the addition of protein A and G Agarose, washed and analyzed by 10% SDS-PAGE (NOVEX), transferred to nitrocellulose and immunoblotted with anti-gp41 monoclonal antibody Chessie 8 (obtained from NIH AIDS Research and Reference Reagent Program), and detected by chemiluminescence (Amersham) and autoradiography.

Surface Immunoprecipitation Assay

Envelope expressing cells can be prepared by co-transfection of human 293T cells with a Rev expression vector (provided by Tris Parslow, University of California, San Francisco, Calif.) and an Env expression vector pSM-WT(HXB2) (provided by Dr. Dan Littman, New York University, New York, N.Y.) using the lipofectamine method (Gibco BRL). U87 cells expressing CD4 with and without CXCR4 chemokine receptor are provided by D. R. Littman. Alternatively, envelope expressing cells can be prepared by the acute infection of laboratory adapted cell lines or primary lymphocytes. Surface Immunoprecipitation: Two days following transfection, $5 \times 10^6$ Env-expressing 293T cells are incubated 1 h at desired temperature in 0.5 ml Dulbecco's Modified Eagle media (DMEM) in the presence or absence of soluble CD4 (Intracell Inc.) (final concentration 4 µM) or appropriate target cells ($5 \times 10^6$ cells in 0.5 ml media). 2 µl of immunosera or hybridoma supernatant is added and allowed to incubate for an additional hour. Cells are washed twice with phosphate buffered saline (PBS) and lysed with 200 µl of lysis buffer (1% Triton X-100, 150 mM NaCl, 50 mM Tris-HCl pH 7.4). The clarified supernatants are incubated 1 h at 4° C. with a mix of 12.5 µM protein A-Agarose/12.5 µM of protein G-Agarose (GIBCO BRL) followed by washing with lysis buffer (3×). Immunoprecipitated complexes are analyzed by 10% SDS-PAGE (NOVEX), transferred to nitrocellulose, and immunoblotted with anti-gp41 monoclonal antibody Chessie 8 (obtained from NIH AIDS Research and Reference Reagent Program), and detected by chemiluminescence (Amersham) and autoradiography.

Immunoprecipitation Studies

The panel of antibodies are tested by surface immunoprecipitation analysis for ability to bind HXB2 gp41 following the interaction of gp120/gp41+ cells with sCD4 or cells expressing various receptor and co-receptor combinations. The surface expressed forms of CD4 and second receptor are furnished by the U87 cell line which has been engineered to selectively express CD4 only, CD4 plus CXCR4, and CD4 plus CCR5. In each case, incubations are performed at 37° C. for various periods of time (initially 5 minutes, 1, 4 and 12 hours as described below), then cooled to 4° C. to limit any further changes while immunoprecipitation is carried out. Immunoprecipitation is performed as described above.

Preparation of Envelope Expressing Cells:

Envelope expressing cells are prepared by infection of U87 cells expressing CD4 and appropriate chemokine receptor with the desired primary virus isolate at high multiplicity of infection (MOI). We have characterized the growth of each of the HIV-1 isolates included in the panel and have determined that all infect and replicate well in the U87 cell line. The level of envelope expression at a given MOI for each virus isolate is determined by the immunoblot procedure described previously. The MOI for each HIV isolate is adjusted to give similar levels of envelope expression in each case. The surface immunoprecipitation assay is carried out as described above.

EXAMPLE 1

Formation of Antibodies

Monoclonal antibodies against the gp41 six-helix bundle are prepared by standard methods. The immunogen used consists of a physical mixture of synthetic peptides modeling the N- and C-helical domains of an envelope protein or glycoprotein that participates in the viral entry event. The immunogen consists of a physical mixture of synthetic peptides modeling the N- and C-helical gp41 domains.

incubate at 25° C. for 3 hr. Following this incubation the cells are washed 4 times with PBS and lysed with 1 ml lysis buffer (1% Triton X-100, 150 mM NaCl, and 50 mM Tris-Cl pH 7.4). The clarified supernatants are incubated with 25 µl Protein A-agarose 125 µl Protein G-agarose (GIBCO BRL) at 4° C. overnight followed by washing 3 times with lysis buffer. Immunoprecipitated complexes are analyzed by 10% SDS-Page gel, transferred to nitrocellulose and immunoblotted with the anti-gp41 monoclonal antibody Chessie 8 (obtained from NIH AIDS Research and Reference Reagent Program) and detected by chemiluminescence and autoradiography. A test compound is considered positive for six-helix bundle disruption if the monoclonal antibody is unable or significantly reduced in its ability to immunoprecipitate the HIV-1 gp41 protein.

EXAMPLE 3

Assay Using Dimethylsuccinylbetulinic Acid as a Viral Fusion Inhibitor

Figure 7B:
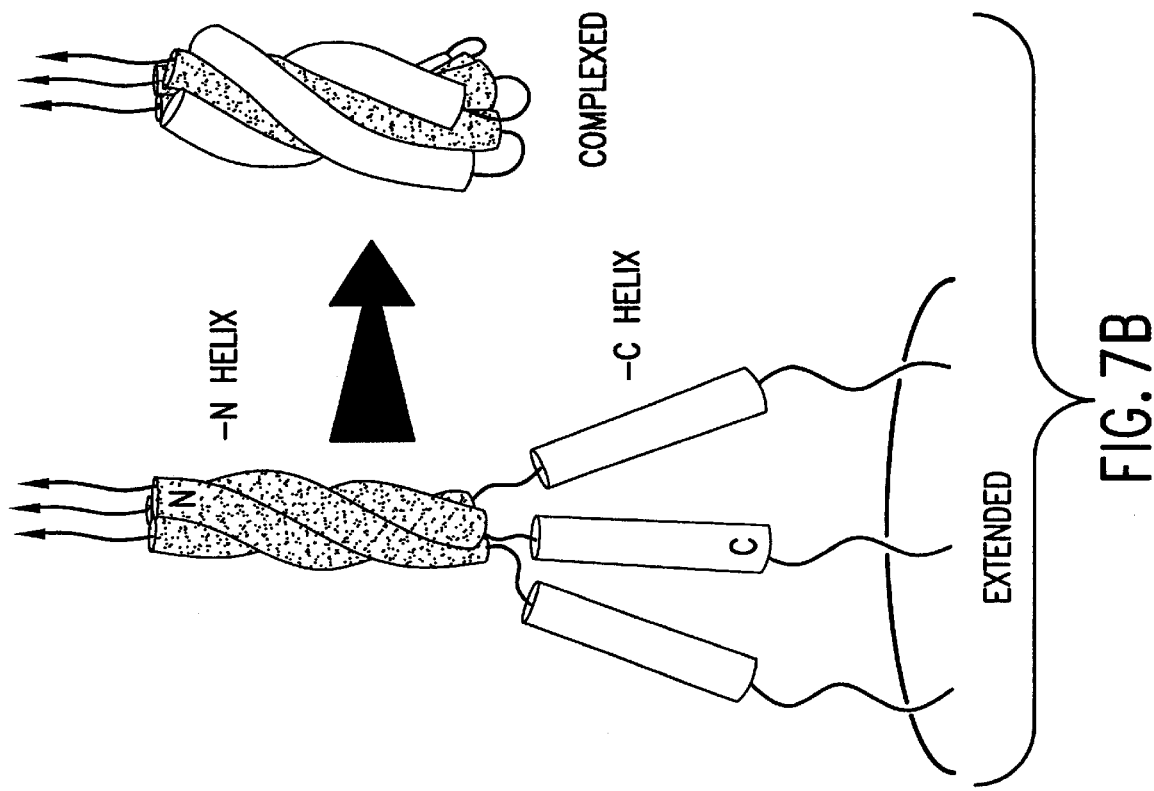
FIGS. 7A and 7B are a schematic representation of the structural and antigenic regions of HIV-1 gp41. These figures also show the conformational changes that these regions typically undergo upon binding of an antibody specific for the gp41 core structure.
Figure 7A:
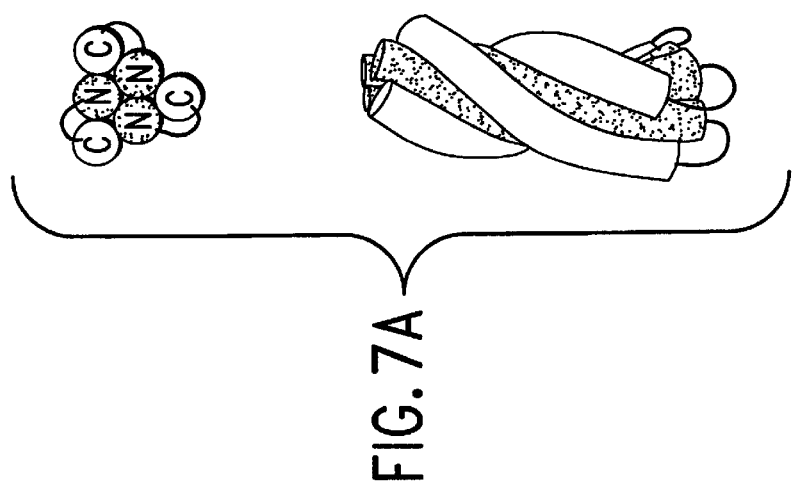

The assay outlined herein, consists of a cell-based system that allows the user to determine if a test compound disrupts HIV-1 gp41 conformational changes necessary for virus entry. The ability of the test compound to disrupt these critical conformational changes is assessed by characterizing the formation of the gp41 core structure. This multimeric structure is formed by the interaction of the N- and C-helical domains of gp41 (FIG. 7b). In one version of this assay, the detection step utilizes antibodies (mono or polyclonal) specific for the core structure.

```
N peptide:  S G I V Q Q Q N N L L R A I E A Q Q H L L Q L T V W G I K Q L Q A R I L.    (SEQ ID NO:3)

C peptide:  W M E W D R E I N N Y T S L I H S L I E E S Q N Q Q E K N E Q E L L          (SEQ ID NO:6)
```

Four balb-c mice are immunized with this mixed construct. Following the initial immunization (100 µg) the animals receive a 100 µg boost on day 14 followed by 50 µg boosts on days 30 and 45. Bleeds occur two weeks following the final boost. The polyclonal sera generated by the immunization of experimental animals are screened by ELISA to characterize binding. Sera samples testing negative for binding by ELISA are abandoned. Animals with sera samples which test positive for binding to the experimental immunogen are candidates for use in monoclonal antibody (MAb) production. Following this initial screen, at least one animal is selected for MAb production. The criteria for this selection is based upon envelope binding patterns against the cognate imrnunogen. Hybridoma supernatants are screened by ELISA against the mixed peptide immunogen. Samples that are ELISA negative are abandoned. Strongly positive samples are screened for their ability to bind viral envelope. Using this approach a panel of monoclonal antibodies is generated against the gp41 six-helix bundle.

EXAMPLE 2

Assay for Viral Fusion Inhibitors

Two days following transfection, intact 293T cells transiently expressing the HIV-1 HXB2 envelope are incubated in the presence of the test compound. At the end of 1 h, 2 µg of soluble CD4 (sCD4) or a cell line expressing CD4 is added. At the end of an additional 1 h, the monoclonal antibody against the six-helix bundle structure is added at a concentration of 10 µg/ml and the mixture is allowed to The following experiments were designed to establish a correlation between the ability of a given compound to disrupt gp41 conformational changes and inhibition of virus replication. The assay is a modified form of an immunoprecipitation (IP) assay and involves incubating the test compound with intact, virus-infected cells expressing the gp120/gp41 envelope complex on their surface. The gp41 conformational changes necessary for virus entry were triggered by the addition of either a soluble form of the target cell receptor, CD4, or the addition of uninfected target cells expressing CD4 on their surface. Antibodies (Ab) specific for the core structure were added. Core structure formation allows Ab binding which in turn allows immunoprecipitation of the Ab/core structure complex which can be characterized and quantitated using gel electrophoresis. Simply put, in the case of core structure formation, (no disruption of conformational changes) gp41 is immunoprecipitated and visualized by a Western blot. In the absence of core structure formation, (disruption of conformational changes) gp41 was not immunoprecipitated or visualized. In these experiments the ability of a test compound to disrupt gp41 conformational changes was measured by determining its effect of core structure formation.

Figure 8:
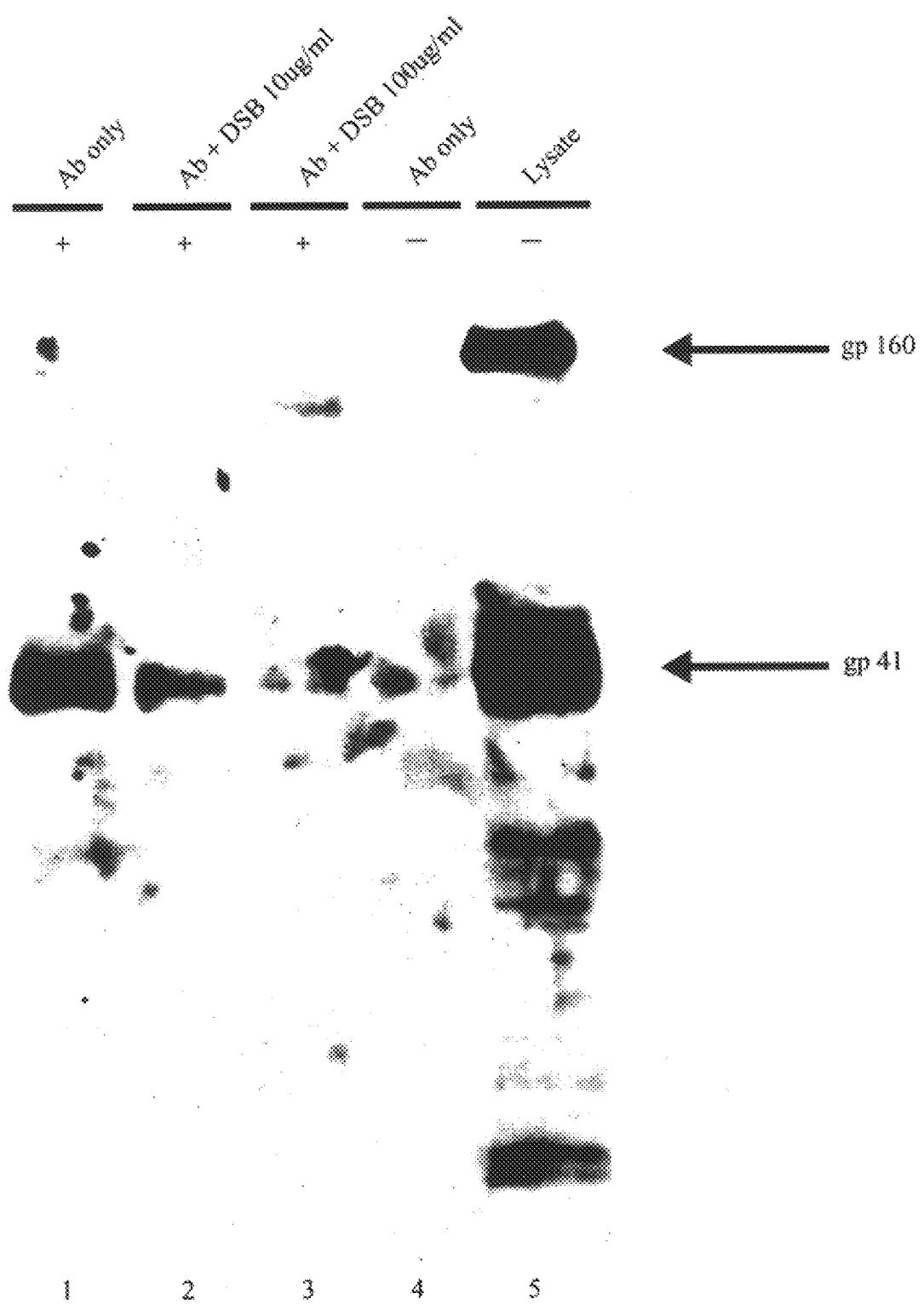
FIG. 8 depicts results from the surface immunoprecipitation experiment on the cell-surface expressed envelope using dimethylsuccinylbetulinic acid (DSB) at two different concentrations: 10 µg/ml and 100 µg/ml.

The ability of several compounds to disrupt the steps leading to core formation was studied as follows:

In this experiment dimethylsuccinylbetulinic acid (DSB) was analyzed at two different concentrations. As can be seen in FIG. 8, the amount of gp41 immunoprecipitated following sCD4 triggering in the absence of test compound (lane 1) is significantly greater than the amount of gp41 immunoprecipitated in the presence of 10 Mg/ml DSB (lane 2). When the test compound is added at 100 μg/ml (lane 3), the amount of gp41 immunoprecipitated is further reduced to a level nearly identical to that recovered in the absence of CD4 triggering (lane 4).

Figure 9:
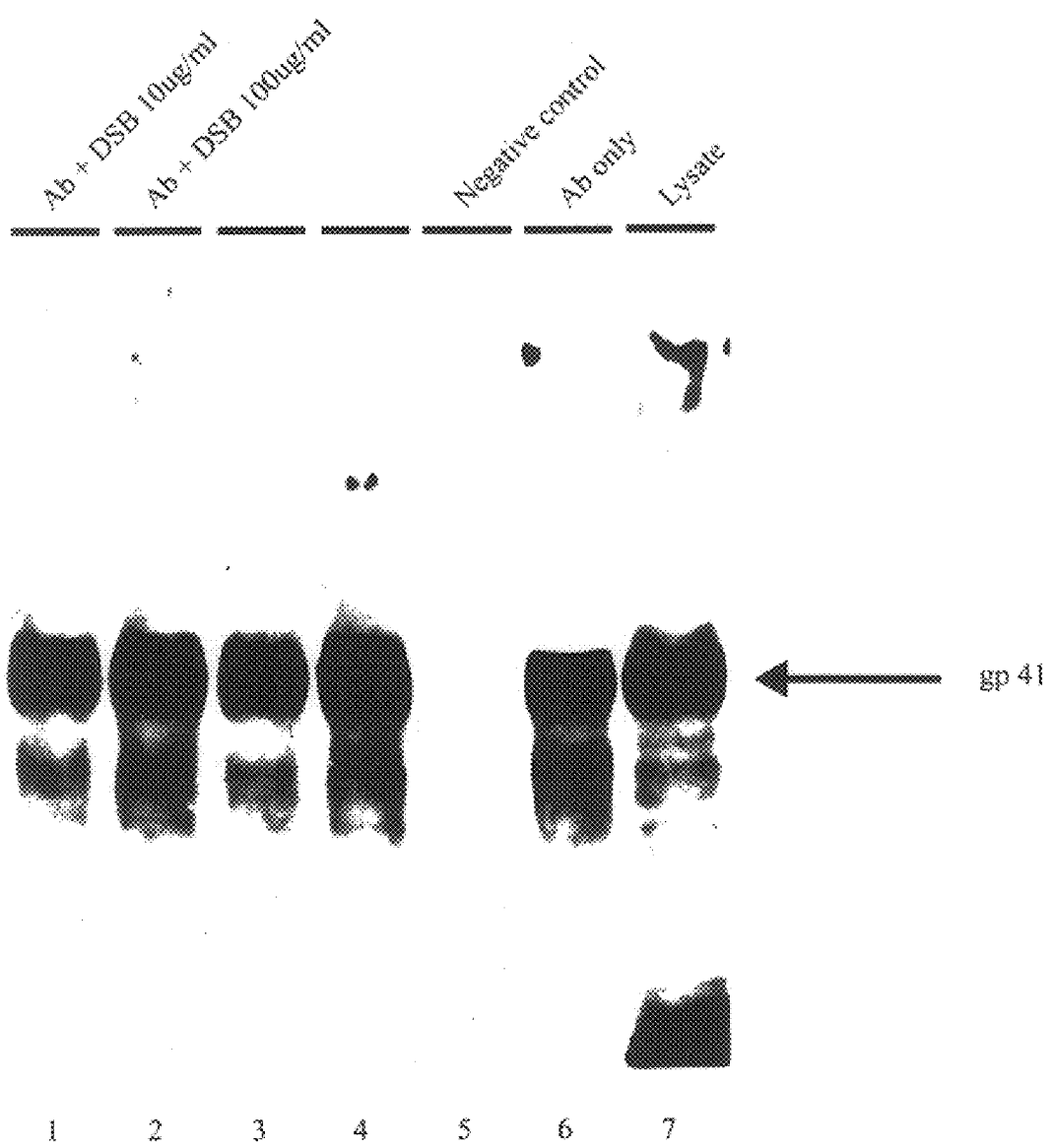
FIG. 9 depicts results from the lysate immunoprecipitation experiment on HIV-1 envelope lysate rather than cell-surface expressed envelope using dimethylsuccinylbetulinic acid (DSB) at two different concentrations: 10 µg/ml and 100 µg/ml.

It was further demonstrated that the DSB results are due to the disruption of core structure formation and not inhibition of antibody binding to the core structure by carrying out an experiment using HIV-1 envelope lysate rather than cell-surface expressed envelope. In this system the core structure exists prior to the addition of the test compound and if the test compound inhibits binding of the antibody to the core structure an effect similar to that observed in the surface IP format would be observed (see FIG. 8). However, no reduction in antibody binding is observed. At DSB concentrations of 10 (lane 1) and 100 μg/ml (lane 2) amounts of gp41 similar to the no compound control (lane 6) are recovered (FIG. 9).

EXAMPLE 4

Preparation of Non-infectious 8E5/LAV Virus Particles

The 8E5/LAV virus particle is the product of a T-cell clone which contains a single, integrated copy of proviral DNA coding for the synthesis of a defective (non-infectious) HIV-1 particle (Folks, T. M., et al., *J. Exp. Med.* 164:280–290 (1986)). This cell line, 8E5LAV, was derived from the A3.01 parent cell line (a CD4+ CEM derivative) infected with LAV (now referred to as HIV-1$_{IIIB}$) by repeated exposure to 5-iodo-2'-deoxyuridine (IUdR). The virus produced by this cloned cell line contained a single base pair addition in the pol gene (position 3241) which gave rise to a non-functional reverse transcriptase resulting in the formation of a non-infectious virus particle (Gendelman, H. E., et al., *Virology* 160:323–329 (1987)). Thorough characterization of this mutant virus revealed that other structural gene products (gag and env) are produced normally and assemble to form a retroviral particle.

The 8E5/LAV cell line is cultured in RPMI 1640 media supplemented with 10% FCS and antibiotics. A two-day culture of cells at an initial density of $5 \times 10^5$ cells/ml will result in culture supernatant with viral particles at a concentration of about $10^8$/ml (determined by electron microscopy). On the day of harvest, the cells are removed by slow speed centrifugation (1500 RPM) and the culture supernatant is clarified by filtration through a 0.45 μm filter. The viral particles are separated from smaller culture byproducts by ultracentrifugation (26000×g, 5 hours, Sorval TFA 20.250 rotor, 4° C.). The viral pellet is resuspended in a 0.1×volume of PBS and quantified by EM (ABI, Columbia, Md.). The viral particles are stored at −70° C. until use.

EXAMPLE 5

Formation of sCD4-Virus Mixture

Non-infectious virions are resuspended to a final concentration of about $10^8$ particles/ml in PBS. Soluble CD4 (MW46,000) is added (final concentration 2 mg/ml) and the mixture allowed to incubate at 37° C. for 4 hours. At the end of this time, the mixture of is separated from non-complexed sCD4 by either size exclusion chromatography (using Sephadex® G-50) or ultracentrifugation on a sucrose gradient.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications, patents and patent applications mentioned in this specification are indicative of the level of skill of those in the art to which the invention pertains. All publications, patents and patent applications are herein incorporated by reference to the same extent as if each individual publication or patent application was specifically and individually indicated to be incorporated by reference in their entirety.

What is claimed is:

1. A method for determining the effect of a test compound on the formation of a conformational intermediate of viral entry and/or fusion, comprising contacting a viral envelope protein or glycoprotein with a triggering agent and a candidate compound to form a mixture, and thereafter measuring the effect that the candidate compound has on the formation of said conformational intermediate.

2. The method according to claim 1, wherein said effect that the candidate compound has on the formation of said conformational intermediate is measured by antibody binding to said conformational intermediate.

3. The method according to claim 1, wherein said effect that the test compound has on the formation of said conformational intermediate is measured by incubating said mixture with specific antibodies to determine whether the amount of antibody binding to a conformational intermediate of viral entry is increased or decreased due to the presence of the test compound.

4. The method according to claim 1, wherein said effect that the candidate compound has on the formation of said conformational intermediate is measured by antibody binding to to viral envelope protein or glycoprotein as it exists prior to contact with a triggering agent.

5. A method for determining the effect of a test compound on the formation of a conformational intermediate of viral entry and/or fusion, comprising
    a. mixing, in an aqueous, buffered solution:
        i. a viral envelope protein or glycoprotein in association with a lipid bilayer, wherein said envelope protein or glycoprotein is necessary and sufficient for viral entry in an intact virus, and wherein said envelope protein or glycoprotein is capable of interacting with one or more receptors on a virus permissive cell;
   ii. one or more virus permissive cells, one or more insoluble or soluble receptors from said virus permissive cells, or a combination thereof; and
   iii. a test compound;

b. measuring the effect of the test compound upon the formation of one or more entry-relevant structures or conformations necessary for virus entry into virus permissive cells.

6. The method according to claim 5, wherein step b is performed by:

adding one or more optionally detectably-labeled antibodies that preferentially bind an epitope that is present in a conformational or structural intermediate in a viral-entry event; and measuring the amount of antibody binding.

7. The method according to claim 5, wherein step b is performed by:

adding one or more optionally detectably-labeled antibodies that preferentially bind an epitope that is present in a viral membrane protein or glycoprotein wherein said viral membrane protein or glycoprotein is not in contact with a triggering agent; and measuring the amount of antibody binding.

8. The method according to claim 7, which further comprises comparing the measured amount of antibody binding to a standard value.

9. The method according to claim 5, wherein viral envelope protein or glycoprotein is from HIV-1, HIV-2, HTLV-I, HTLV-II, respiratory syncytial virus (RSV), parainfluenza virus type 3 (HPIV-3), Newcastle disease virus, feline immunodeficiency virus (FIV), human influenza viruses, or measles virus.

10. The method according to claim 5, wherein said lipid bilayer is provided in the form of cells, virions, pseudovirions, membrane vesicles or liposomes.

11. The method according to claim 5, wherein reagent ii is one or more lymphocytes.

12. The method according to claim 5, wherein reagent ii is one or more of soluble CD4 receptors, insoluble CD4 receptors, chemokine receptors or mixtures thereof.

13. A method for determining the effect of a test compound on the formation of a conformational intermediate of HIV-1 viral entry and/or fusion, comprising:

a. mixing, in an aqueous, buffered solution:
   i. HIV-1 envelope glycoproteins gp120/gp41 or fragments thereof in association with a lipid bilayer;
   ii. one or more lymphocytes, or one or more insoluble or soluble receptors from said lymphocytes, or a combination thereof; and
   iii. a test compound;

b. measuring the effect of the test compound upon the formation of one or more entry-relevant structures or conformations necessary for virus entry into virus permissive cells.

14. The method according to claim 13, wherein said lipid bilayer is provided in the form of cells, virions, pseudovirions, membrane vesicles or liposomes.

15. The method according to claim 13, wherein reagent ii is one or more of soluble CD4 receptors, insoluble CD4 receptors, chemokine receptors or mixtures thereof.

16. The method according to claim 13, wherein said HIV-1 envelope glycoproteins gp120/gp41 or fragments thereof are provided in the form of non-infectious viral particles.

17. The method according to claim 13, wherein said measuring step is performed by:

adding one or more optionally detectably-labeled antibodies that bind an epitope that is a structural or conformational intermediate in a viral-entry event;

and measuring the amount of antibody binding.

18. The method according to claim 13, wherein said measuring step is performed by:

adding one or more optionally detectably-labeled antibodies that preferentially bind an epitope that is present in a viral membrane protein or glycoprotein wherein said viral membrane protein or glycoprotein is not in contact with a triggering agent; and measuring the amount of antibody binding.

19. The method according to claim 6, which further comprises comparing the measured amount of antibody binding to a standard value.

* * * * *